US009969864B2

(12) United States Patent
Peter et al.

(10) Patent No.: US 9,969,864 B2
(45) Date of Patent: May 15, 2018

(54) LIGHT STABILIZERS

(71) Applicant: BASF SE, Ludwigshafen (DE)

(72) Inventors: Wolfgang Peter, Altluβheim (DE); Adalbert Braig, Binzen (DE); Ulrich Berens, Binzen (DE); Kai-Uwe Schöning, Oberwil (CH); Markus Grob, Reinach (CH); Cinzia Tartarini, Basel (CH); Tania Weyland, Widensolen (FR)

(73) Assignee: BASF SE, Ludwigshafen am Rhein (DE)

( * ) Notice: Subject to any disclaimer, the term of this patent is extended or adjusted under 35 U.S.C. 154(b) by 79 days.

(21) Appl. No.: 14/903,645

(22) PCT Filed: Jul. 3, 2014

(86) PCT No.: PCT/IB2014/062823
§ 371 (c)(1),
(2) Date: Jan. 8, 2016

(87) PCT Pub. No.: WO2015/004580
PCT Pub. Date: Jan. 15, 2015

(65) Prior Publication Data
US 2016/0168356 A1    Jun. 16, 2016

(30) Foreign Application Priority Data

Jul. 8, 2013  (EP) ..................................... 13175595

(51) Int. Cl.
| | | |
|---|---|---|
| *C08K 5/3435* | (2006.01) |
| *C07D 211/46* | (2006.01) |
| *C09D 123/06* | (2006.01) |
| *C09D 123/12* | (2006.01) |
| *C09D 127/06* | (2006.01) |
| *C09D 133/12* | (2006.01) |
| *C09D 155/02* | (2006.01) |
| *C09D 167/06* | (2006.01) |
| *C09D 169/00* | (2006.01) |
| *C09D 175/04* | (2006.01) |
| *C08K 5/00* | (2006.01) |
| *C08K 5/34* | (2006.01) |

(52) U.S. Cl.
CPC .......... *C08K 5/3435* (2013.01); *C07D 211/46* (2013.01); *C08K 5/005* (2013.01); *C09D 123/06* (2013.01); *C09D 123/12* (2013.01); *C09D 127/06* (2013.01); *C09D 133/12* (2013.01); *C09D 155/02* (2013.01); *C09D 167/06* (2013.01); *C09D 169/00* (2013.01); *C09D 175/04* (2013.01)

(58) Field of Classification Search
CPC ........................ C07D 211/46; C08K 5/3435
USPC ........................................... 524/99; 546/242
See application file for complete search history.

(56) References Cited

U.S. PATENT DOCUMENTS

| | | |
|---|---|---|
| 4,001,190 A | 1/1977 | Tanikella et al. |
| 4,021,432 A | 5/1977 | Holt et al. |
| 4,046,737 A | 9/1977 | Holt et al. |
| 4,049,647 A | 9/1977 | Holt et al. |
| 4,055,536 A | 10/1977 | Soma et al. |
| 4,131,599 A | 12/1978 | Brunetti et al. |
| 4,231,921 A | 11/1980 | Moser |
| 4,325,863 A | 4/1982 | Hinsken et al. |
| 4,338,244 A | 7/1982 | Hinsken et al. |
| 4,344,876 A | 8/1982 | Berner |
| RE31,342 E | 8/1983 | Holt et al. |
| 4,507,463 A | 3/1985 | Orban |
| 4,535,145 A | 8/1985 | Troxler et al. |
| 4,536,581 A | 8/1985 | Cantatore et al. |
| 4,731,448 A | 3/1988 | Issler et al. |
| 4,942,238 A | 7/1990 | Rytz et al. |
| 5,068,335 A | 11/1991 | Kress et al. |
| 5,175,312 A | 12/1992 | Dubs et al. |
| 5,216,052 A | 6/1993 | Nesvadba et al. |
| 5,252,643 A | 10/1993 | Nesvadba |
| 5,356,966 A | 10/1994 | Nesvadba |
| 5,367,008 A | 11/1994 | Nesvadba |
| 5,428,162 A | 6/1995 | Nesvadba |
| 5,428,177 A | 6/1995 | Nesvadba |
| 5,488,117 A | 1/1996 | Nesvadba |
| 5,856,494 A | 1/1999 | Julius et al. |
| 6,353,107 B1 | 3/2002 | Kramer et al. |
| 7,214,742 B2 | 5/2007 | Bolle et al. |
| 7,332,105 B2 | 2/2008 | Braig et al. |
| 7,687,554 B2 | 3/2010 | Schellenberg et al. |
| 7,695,643 B2 | 4/2010 | Fritzsche et al. |
| 8,262,949 B2 | 9/2012 | Fritzsche et al. |
| 8,389,719 B2 | 3/2013 | Vogel et al. |
| 8,586,735 B2 | 11/2013 | Vogel et al. |
| 2009/0117394 A1 | 5/2009 | Vogel et al. |
| 2010/0062270 A1 | 3/2010 | Jahn et al. |
| 2012/0027960 A1 | 2/2012 | Xu et al. |
| 2015/0079412 A1 | 3/2015 | Jahn et al. |
| 2016/0009952 A1 | 1/2016 | Wood et al. |
| 2016/0215151 A1 | 7/2016 | Ehlis et al. |

FOREIGN PATENT DOCUMENTS

| | | | | |
|---|---|---|---|---|
| CA | 1317963 | * | 5/1993 | ........... C07D 211/46 |
| DE | 2258752 A1 | | 6/1973 | |

(Continued)

OTHER PUBLICATIONS

International Search Report for PCT/IB2014/062823 dated Nov. 26, 2014.

(Continued)

*Primary Examiner* — Fred M Teskin

(74) *Attorney, Agent, or Firm* — Drinker Biddle & Reath LLP

(57) ABSTRACT

The present invention relates to symmetric diesters of hydroxyalkyl-4-hydroxy-tetraalkylpiperidine compounds and their use as light stabilizers. They are compatible with and soluble in coating formulations of different polarity.

20 Claims, No Drawings

(56) References Cited

FOREIGN PATENT DOCUMENTS

| | | |
|---|---|---|
| DE | 26 21 841 A1 | 12/1976 |
| DE | 26 30 798 A1 | 2/1977 |
| DE | 29 10 761 A1 | 10/1979 |
| DE | 4316611 A1 | 11/1993 |
| DE | 4316622 A1 | 11/1993 |
| DE | 4316876 A1 | 11/1993 |
| EP | 000 487 A1 | 2/1979 |
| EP | 0 004 104 A2 | 9/1979 |
| EP | 126 028 A2 | 11/1984 |
| EP | 135 470 A1 | 3/1985 |
| EP | 225 850 A1 | 6/1987 |
| EP | 0 290 387 A1 | 11/1988 |
| EP | 517 103 A1 | 12/1992 |
| EP | 0589839 A1 | 3/1994 |
| EP | 0591102 A1 | 4/1994 |
| EP | 0 825 182 A1 | 2/1998 |
| EP | 1291384 A1 | 3/2003 |
| EP | 1 642 892 A1 | 4/2006 |
| JP | 4370101 B2 | 11/2009 |
| WO | WO-2013022609 A1 | 2/2013 |

OTHER PUBLICATIONS

Pritchard, G. Plastics additives: an A-z reference, Springer p. 354-355, (1998).

* cited by examiner

LIGHT STABILIZERS

CROSS-REFERENCE TO RELATED APPLICATIONS

This application is a national stage application (under 35 U.S.C. § 371) of PCT/IB2014/062823, filed Jul. 3, 2014, which claims benefit of European Application No. 13175595.1, filed Jul. 8, 2013, both of which are incorporated herein by reference in their entirety.

The present invention relates to symmetric diesters of hydroxyalkyl-4-hydroxy-tetraalkylpiperidine compounds and their use as light stabilizers.

Many materials and in particular coatings are exposed to light, heat, and temperature changes (i.e., weathering). This may lead to undesired alterations such as color deviation, loss of gloss or even to cracking and delamination. These alterations are often mainly due to light, in particular UV-light, which leads to photochemically induced degradation reactions.

Light stabilization of coatings is therefore crucial in order to maintain their appearance and gloss, which are expected to remain unchanged for many years. The induction of these degradation reactions is prevented by adding a compound that absorbs UV-light. The compound that absorbs UV-light reduces the intensity of UV-light within the coating. However, according to the Lambert-Beer-Law, a significant reduction of UV-Intensity can only be achieved in the part of the coating that is not at the surface. No significant reduction of UV-intensity is achieved at the surface of the coating. Degradation reactions are thus induced at the surface of a coating even if a compound that absorbs UV-light is present.

For this reason a HALS (hindered amine light stabilizer) needs to be added as a complementary stabilizer. In most cases it is a derivative of 2,2,6,6-tetramethylpiperidine. HALS compounds scavenge efficiently free radicals formed at the coating surface, where minor or no protection through the UVA is given. This process has been extensively studied and is essentially a cyclic chain breaking antioxidant process which is known as the Denisov cycle.

HALS derivatives such as e.g. Tinuvin 770 or derivatives of N-alkyl functionalized HALS such as Tinuvin 292 are relative strong bases. They undergo acid/base interactions with components in the formulation of coating systems such as acid catalysts, biocides, surfactants, certain metal catalysts (e.g. co-catalysts) or pigments with acidic surface treatment. This results in limited formulation stability, cure retardation or inhibition or the deactivation of other additives. Furthermore, protonation of HALS leads to the formation of inactive HALS ammonium salts which adversely affect their stabilizing activity (see G. Pritchard, Plastics additives: an A-Z reference, Springer 1998, p. 354).

In order to overcome this problem, N-alkoxyderivatives ("NOR's") such as Tinuvin 123 (Scheme 1) and 1-alkyloyl-2,2,6,6-tetramethylpiperidine derivatives e.g. Hostavin 3058 (Scheme 1) were developed. These are applicable in acidic formulations due to their low basicity. However, their production is expensive and the compatibility of e.g. Tinuvin 123 in polar formulations is insufficient resulting in exudation. Furthermore, the performance of N-acyl-HALS derivatives is inferior in comparison to "NOR's" under harsh exposure conditions due to the slow formation of the nitroxyl radical.

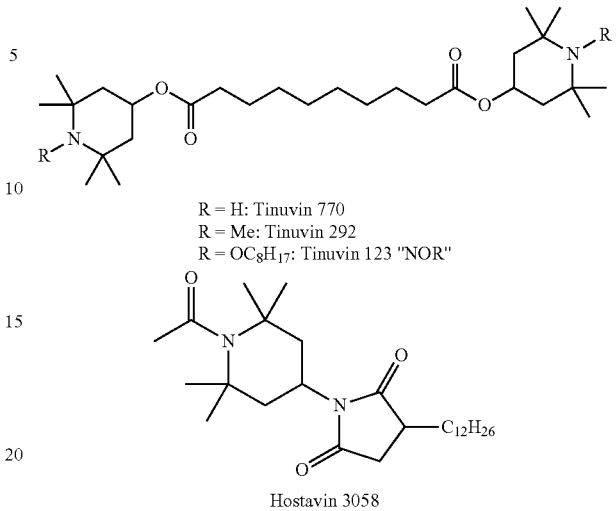

R = H: Tinuvin 770
R = Me: Tinuvin 292
R = OC$_8$H$_{17}$: Tinuvin 123 "NOR"

Hostavin 3058

A comparatively cheap HALS derivative with lower basicity is 1-(2-hydroxy-ethyl)-2,2,6,6-tetramethyl-piperidin-4-ol ("HE-HTMP" 1). This compound can for example be obtained by N-alkylation of 4-hydroxy-2,2,6,6-tetramethylpiperidine 2 (Scheme 2) with ethylene oxide. However, 1 is highly polar and hydrophilic. It is thus incompatible with or insoluble in formulations of low polarity. Due to its high water solubility it will be leached out quickly under weathering conditions resulting in insufficient UV stabilization of the polymer matrix.

Oligomeric HALS derivatives, e.g. Tinuvin 622, as described in EP 126 028, EP 135 470, were developed for specific use in plastics and are not prone to leaching. However, these oligomeric derivatives of 1 are not compatible with typical coating formulations as their solubility in these formulations is insufficient.

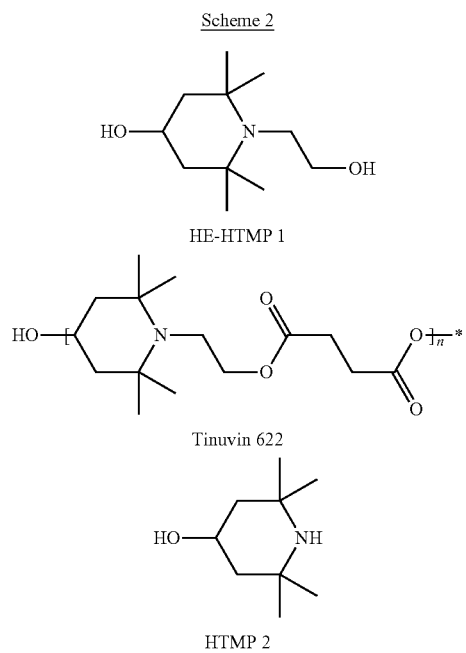

HE-HTMP 1

Tinuvin 622

HTMP 2

Esters of 1 with acetoacetic acid are known from EP 000 487 A1 and have been claimed as light stabilizers for polypropylene, polyethylene, poly ethylene isophthalate (bulk or fibers). Such esters can—due to the presence of the beta-ketoester functionality form metal chelates which can be used in similar applications.

EP 1 642 892 describes hindered amine light stabilizers that are suitable to stabilize resins. They are obtained by adding a lactone to 2,2,6,6-tetramethyl-piperidin-4-ol. U.S. Pat. No. 4,344,876 discloses light stabilizers on the basis of 2,2,6,6-tetramethyl-piperidin-4-ol in which the 4-hydroxy group is esterified and the nitrogen atom is substituted with a hydrocarbyl group. DE 2258752 describes a large group of light stabilizers on the basis of 2,2,6,6-tetramethyl-piperidin-4-ol which may have a broad variety of substituents at the 4-hydroxy group and at the nitrogen atom.

Light stabilizers that are symmetrical diesters of HE-HTMP derived from aromatic carboxylic acid esters are known from EP 517 103, WO 2013/022609, and US 2012/027960. For efficient applicability in coating applications, a light stabilizer has to fulfill a broad range of properties: compatibility with coating formulations of different polarity (i.e. solubility in coating compositions that are based on polar to non-polar solvents, no exudation from the coating), no interference with curing, no impact on the initial color or the initial appearance (e.g. gloss) of the coating, an improvement of resistance towards UV-light that is comparable to established light stabilizers, low volatility, and being liquid under normal conditions, which allows easy incorporation into coating formulations. Broad compatibility along with good solubility in coating formulations of different polarity is a requirement which so far has not been solved.

The problem underlying the invention was therefore to provide light stabilizers that are compatible with and soluble in coating formulations of different polarity. Furthermore, it is desirable that the light stabilizers meet the other requirements mentioned above as well.

This problem is solved by a compound having the formula (I)

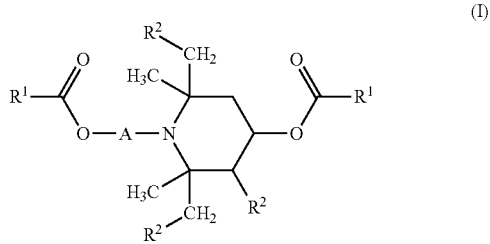

wherein
A —CH($R^3$)—CH$_2$— or —CH$_2$—CH($R^3$)—;
each $R^1$ is the same and is selected from:
  $C_1$-$C_{21}$ alkyl;
  $C_3$-$C_7$ cycloalkyl;
  —CH$_2$—$R^5$, wherein $R^5$ is acyclic $C_2$-$C_{20}$ hydrocarbyl having one, two, or three double bonds;
  $C_1$-$C_{21}$ alkyl substituted with at least one substituent selected from $C_1$-$C_4$ alkoxy, —OH or —CN;
  $C_3$-$C_7$ cycloalkyl substituted with at least one substituent selected from $C_1$-$C_4$ alkyl, $C_1$-$C_4$ alkoxy, —OH or —CN; and
  $C_4$-$C_{21}$ alkyl substituted with —CO—$R^4$, wherein $R^4$ is $C_1$-$C_4$ alkyl; and
$R^2$ is selected from H and $C_1$-$C_3$ alkyl; and
$R^3$ is H or $C_1$-$C_4$ alkyl.

The terms "alkylene", "alkyl", "hydrocarbyl" and "alk", for example in "alkoxy" as used herein relate to branched or straight carbon chains.

The term "alkyl" (also in "alkoxy" etc.) includes, for example, methyl, ethyl, propyl, isopropyl, n-butyl, isobutyl, sec.-butyl, tert.-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, 1,1,3,3-tetramethylbutyl, nonyl, decyl, n-undecyl, n-dodecyl, n-tridecyl, iso-tridecyl, n-tetradecyl, n-hexadecyl, n-octadecyl, n-eicosyl, etc.

The term "hydrocarbyl" means an acyclic straight or branched carbon chain of 2 to 20 carbon atoms.

The term "cycloalkyl" means a saturated cyclic hydrocarbon with 3 to 7 ring carbon atoms. Cycloalkyl groups are cyclopropyl, cyclobutyl, cyclopentyl, cyclohexyl and cycloheptyl with cyclopentyl and cyclohexyl being preferred.

In an embodiment, each $R^1$ is selected from $C_1$-$C_{21}$ alkyl, preferably from $C_1$-$C_{17}$ alkyl, and in particular from $C_1$-$C_{12}$ alkyl. In a further embodiment, each $R^1$ is selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, and $C_{17}$ alkyl, or $C_3$-$C_7$ cycloalkyl, in particular $C_3$-$C_7$ cycloalkyl. In a further embodiment, said alkyl groups are branched.

In a preferred embodiment, each $R^1$ is selected from methyl, ethyl, isopropyl, tert-butyl, n-pentyl, 1-ethylpentyl, 1,13,3-tetramethylbutyl, 2,4,4-trimethylpentyl, 1-propylhexyl, n-undecyl, n-tridecyl, n-pentadecyl, n-heptadecyl, cyclopentyl, cyclohexyl, 2-methoxyethyl, methoxymethyl and acetoethyl. 1-Ethylpentyl, 2,4,4-trimethylpentyl, and 1-propylhexyl are particularly preferred.

In another embodiment, each $R^1$ is selected from $C_1$-$C_{21}$ alkyl substituted with at least one substituent selected from $C_1$-$C_4$ alkoxy and —OH.

In another embodiment, both groups $R^1$ are the same.

In any of the above embodiments, $R^2$ is selected from H and $C_1$-$C_3$ alkyl, preferably from H and methyl. Embodiments wherein $R^2$ is H are particularly preferred.

In any of the above embodiments, A is typically selected from —CH$_2$—CH$_2$—, #—CH(CH$_3$)—CH$_2$—, or #—CH$_2$—CH(CH$_3$)—, #—CH$_2$—CH(CH$_2$—CH$_3$)—, #—CH(CH$_2$—CH$_3$)—CH$_2$—, #—CH$_2$—CH(CH$_2$—CH$_2$—CH$_3$)—, #—CH(CH$_2$—CH$_2$—CH$_3$)—CH$_2$—, #—CH$_2$—CH(CH$_2$—CH$_2$—CH$_2$—CH$_3$) and #—CH$_2$—CH(CH$_2$—CH$_2$—CH$_2$—CH$_3$). Embodiments wherein A is —CH$_2$—CH$_2$—, #—CH(CH$_3$)—CH$_2$—, or #—CH$_2$—CH(CH$_3$)— are particularly preferred. Embodiments wherein A is —CH$_2$—CH$_2$— or #—CH(CH$_3$)—CH$_2$— are more preferred. (# denotes the attachment to the oxygen atom). Embodiments wherein A is —CH$_2$—CH$_2$— are most preferred.

A further embodiment are compounds of formula (I), wherein both groups $R^1$ are the same and are selected from methyl, ethyl, isopropyl, tert-butyl, n-pentyl, 1-ethylpentyl, 1,13,3-tetramethylbutyl, 2,4,4-trimethylpentyl, 1-propylhexyl, n-undecyl, n-tridecyl, n-pentadecyl, n-heptadecyl, cyclopentyl, cyclohexyl, 2-methoxyethyl, methoxymethyl and acetoethyl, $R^2$ is H and A is —CH$_2$—CH$_2$— or #—CH(CH$_3$)—CH$_2$—, in particular —CH$_2$—CH$_2$—.

A further embodiment of the present invention is a composition comprising a) an organic material, preferably a natural or synthetic organic polymer, in particular polyethylene, polypropylene, polyurethane, a styrenic polymer or polyvinylchloride, and b) a compound of the formula (I) as defined above.

The organic material is in general a polymer including resins. Examples of component a) are 1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkylmethacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxycaproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates,

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

31. Aqueous emulsions of natural or synthetic rubber, e.g. natural latex or latices of carboxylated styrene/butadiene copolymers.

The compound of the formula (I) may be present in the organic material, preferably polyethylene, polypropylene, polyurethane, styrenics polymer or polyvinylchloride, in an amount of preferably 0.005 to 20%, in particular 0.01 to 2% or 0.05 to 1%, relative to the weight of the organic material.

The stabilizer of the formula (I) can be incorporated into the organic material to be stabilized by known methods, for example before or during shaping or by applying the dissolved or dispersed stabilizer to the organic material, if necessary with subsequent evaporation of the solvent. The stabilizer can be added to the organic material in the form of a powder, granules or a masterbatch, which contains said stabilizer in, for example, a concentration of from 2.5 to 25% by weight.

The organic materials stabilized according to this invention can be used in a wide variety of forms, for example as films, fibres, tapes, moulding compositions, profiles or as binders for paints, adhesives or putties.

In an embodiment the composition is a coating composition, i.e. the organic material is suitable for coating purposes. The composition may be solvent based or water based. Typical examples of organic solvents are aliphatic, aromatic or cycloaliphatic hydrocarbons, alcohols, glycols, esters, acetates and ketones. In another embodiment, the composition is an automotive coating composition.

The coating composition is preferably a laquer, in particular a stoving laquer which is used for coating automobiles (automobile finishing lacquers), for example stoving lacquers comprising alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

The coating composition may also comprise an epoxy, epoxy-polyester, vinyl, alkyd, acrylic and polyester resin, optionally modified with silicon, isocyanate or isocyanurate (non-acid catalyzed thermoset resins). The epoxy and epoxy-polyester resins are crosslinked with conventional crosslinkers such as acids, acid anhydrides or amines. Correspondingly, epoxide may be utilized as the crosslinking agent for various acrylic or polyester resin systems that have reactive groups on the backbone structure.

A specific coating composition of the present invention is a radiation curable composition comprising ethylenically unsaturated monomers or oligomers and a polyunsaturated aliphatic oligomer.

A specific coating composition of the present invention is a powder coating composition.

Particularly preferred coating compositions comprise at least one additive selected from 2-(2'-hydroxyphenyl)benzotriazoles, 2-(2-hydroxyphenyl)-1,3,5-triazines, 2-hydroxybenzophenones, and oxanilides.

Another embodiment of the present invention is a molded material comprising a compound having the formula (I) and at least one polymer.

In the composition, the compound having the formula (I) is in general present in an amount from 0.02% to 20%, preferably from 0.1% to 10% and more preferably from 0.25% to 5% by weight, based on the weight of the based on the solids content (polymer or resin solids) of the coating composition.

Additionally the compositions according to the present invention, in particular the coating compositions, may optionally comprise at least one further additive; examples of additives are listed below:

1. Antioxidants 1.1 Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-('-methyltridec-1'-yl)phenol and mixtures thereof.

1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3 Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4 Tocopherols, for example α-tocopherol, β-tocopherol, γ-tocopherol, δ-tocopherol and mixtures thereof (vitamin E).

1.5 Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3, 5-dimethyl-2-hydroxyphenyl)butane, 2,2-bis(3,5-di-tertbutyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7 O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8 Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)-malonate, di-dodecylmercaptoethyl-2,2-bis(3,5-di-tert-butyl-4-hydroxybenzyl)-malonate, bis[4-(1, 1,3,3-tetramethylbutyl)phenyl]-2,2-bis(3,5-di-tert-butyl-4-hydroxybenzyl)-malonate.

1.9 Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10 Triazine derivatives, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3, 5-dicyclohexyl-4-hydroxybenzyl)isocyanurate.

1.11 Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12 Acylaminophenols, for example 4-hydroxylauranilide, 4-hydroxystearanilide, octyl N-(3,5-di-tert-butyl-4-hydroxyphenyl)carbamate.

1.13 Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15 Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyl-oxy)ethyl]oxamide (Naugard®XL-1, supplied by Uniroyal).

1.18 Ascorbic acid (vitamin C)

1.19 Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV absorbers and light stabilizers 2.1 2-(2'-Hydroxyphenyl)benzotriazoles, for example 2-(2'-hydroxy-5'-methylphenyl)benzotriazole, 2-(3',5'-ditert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole, 6-butyl-2-[2-hydroxy-3-(1-methyl-1-phenylethyl)-5-(1, 1,3,3-tetramethylbutyl)phenyl]-pyrrolo[3,4-f]benzotriazole-5,7(2H,6H)-dione.

2.2 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3 Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4 Acrylates, for example ethyl α-cyano-β,β-diphenylacrylate, isooctyl α-cyano-β,β-diphenylacrylate, methyl α-carbomethoxycinnamate, methyl α-cyano-β-methyl-β-methoxycinnamate, butyl α-cyano-β-methyl-β-methoxycinnamate, methyl α-carbomethoxy-β-methoxycinnamate, N-(β-carbomethoxy-β-cyanovinyl)-2-methylindoline, neopentyl tetra(α-cyano-β,β-diphenylacrylate.

2.5 Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Other sterically hindered amines, for example bis(2, 2,6,6-tetramethyl-4-piperidyl)-sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7 Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropopropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyidialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:
Tris(2,4-di-tert-butylphenyl) phosphite (Irgafos®168, Ciba Specialty Chemicals Inc.), tris(nonylphenyl) phosphite,

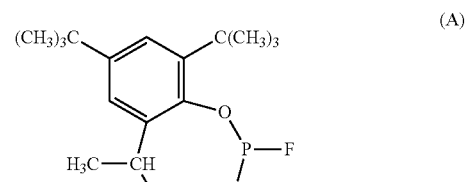

(A)

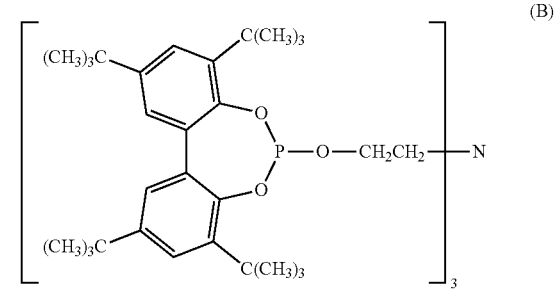

(B)

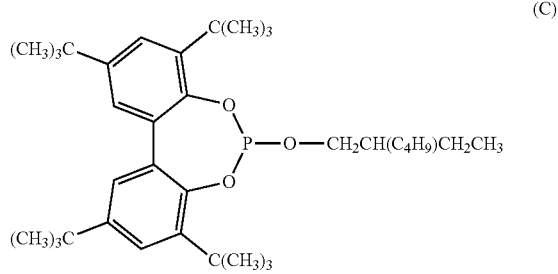

(C)

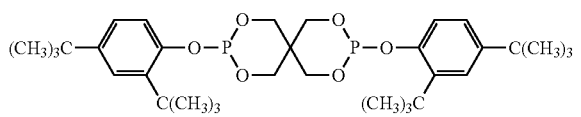

(D)

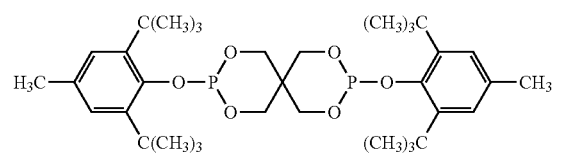

(E)

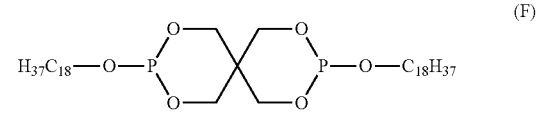

(F)

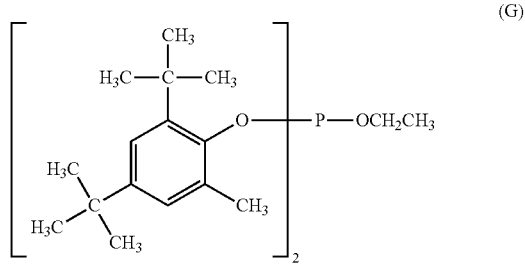

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N- dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alphamethylnitrone, N-octyl-alpha-heptylnitrone, N-lauryl-alpha-undecylnitrone, N-tetradecyl alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticizers, lubricants, emulsifiers, pigments, rheology additives, catalysts, flow-control agents, optical brighteners, flame retardants, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

The weight ratio of the compound of the formula (I) to the total amount of the conventional additives can be, for example, 100:1 to 1:1000 or 10:1 to 1:100 or 10:1 to 1:10.

The sterically hindered amines listed above under 2.6 are particularly preferred.

A further embodiment of the present invention is a method for stabilizing an organic material against degradation induced by light, heat or oxidation, which comprises incorporating a compound of the formula (I) as defined above into the organic material.

Another embodiment of the present invention is the use of a compound having the formula (I) as a light stabilizer or for preparing a coating on a substrate.

The preparation of the coating on a substrate preferably includes the application of the above coating composition to the substrate. The application of the coating composition to the substrate is done by customary methods, preferably by brushing, spraying, pouring, dipping or electrodeposition (see also Ullmann's Encyclopedia of Industrial Chemistry, 5th Edition, Vol. A18, pp. 491-500).

The substrate is preferably selected from an underlaying coatings (referred to in the following as "substrate coating"), or from metals, metal alloys, woods, plastics, and ceramics.

The substrate coating may consist of one or more layers of coating, preferably of 1 to 5 layers. Preferably, the substrate coating comprises at least one resin and at least one pigment.

An aspect of the present invention is an automotive coating that comprises a metal substrate and a coating comprising a) a primer coat which is electrodeposited onto a metal substrate;

b) at least one pigmented base coat which is in direct contact with the primer coat, and c) a clear coat that is in direct contact with the pigmented base coat and comprises a compound having the formula (I).

Preferably, the automotive coating, preferably coat c), further comprises at least one additive selected from 2-(2'-hydroxyphenyl)benzotriazoles, 2-(2-hydroxyphenyl)-1,3,5-triazines, 2-hydroxybenzophenones, and oxanilides or combinations thereof.

The materials stabilized according to the present invention may be processed or transformed, for example, by one of the following methods or combinations thereof:

Injection blow molding, extrusion, blow molding, rotomolding, in mold decoration (back injection), slush molding, injection molding, co-injection molding, forming, compression molding, pressing, film extrusion (cast film; blown film), fiber spinning (woven, non-woven), drawing (uniaxial, biaxial), annealing, deep drawing, calandering, mechanical transformation, sintering, coextrusion, coating, lamination, crosslinking (radiation, peroxide, silane), vapor deposition, weld together, glue, vulkanization, thermoforming, pipe extrusion, profile extrusion, sheet extrusion; sheet casting, spin coating, strapping, foaming, recycling/rework, extrusion coating, visbreaking (peroxide, thermal), fiber melt blown, spun bonded, surface treatment (corona discharge, flame, plasma), sterilization (by gamma rays, electron beams), cast polymerization (R&M process, RAM extrusion), gel-coating, tape extrusion, GMT-process, SMC-process, plastisol, and dipping (PVC, latex).

The compositions according to the present invention may be used for the preparation of the following devices:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, handy, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), BOPP, BOPET, bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (for eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, TiO2, mica, nanocomposites, dolomite, silica, silicates, glass, asbestos).

The compound having the formula (I) may be prepared by any method known to a person skilled in the art. A suitable method includes the steps a), b), c) and d) shown below ($R^1$, A and $R^2$ are as defined above):

Aluminium alcoholates and titanium alcoholates are preferred. Titanium alcoholates and mixtures thereof, such as tetrabutyl orthotitanate and tetraisopropyl orthotitanate, and aluminium tri-isopropylate, and also mixtures of titanates and aluminates are particularly preferred.

Alternatively, activated derivatives of carboxylic acids such as acid chlorides and anhydrides can be used in step d). Conveniently, the reaction is carried out in the presence of a base. Suitable bases are nitrogen bases such as imidazole or p-dialkylamino pyridine derivatives such as p-dimethylamino pyridine.

The compounds of the invention may contain a low amount (for example less than 10%, less than 5% and less than 1% by weight) of the corresponding monoesters. If desired, mono and diesters can be separated by conventional methods, for example by chromatography.

The following examples illustrate the invention without limiting it. All percentages and parts are by weight, unless stated otherwise.

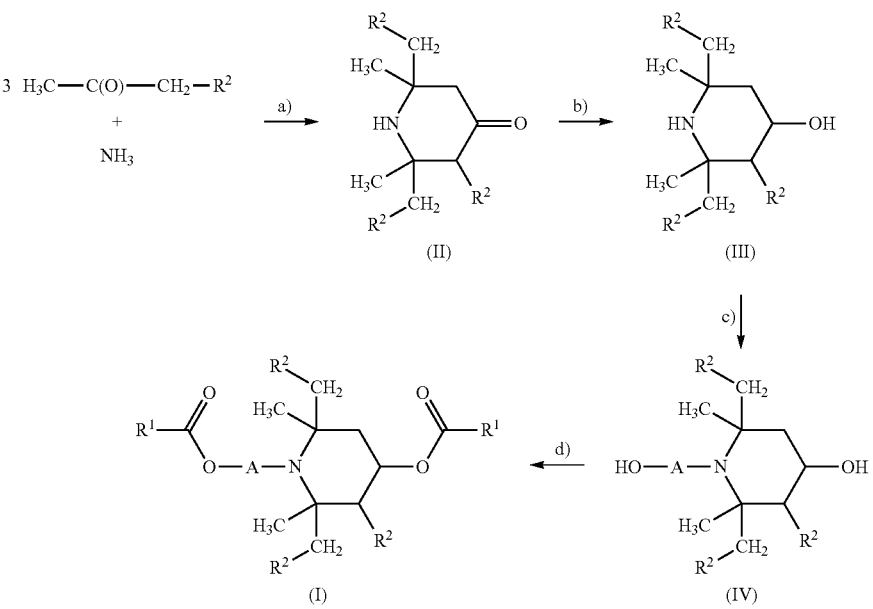

Suitable methods for step a) are described, for example, in EP 0 825 182 A1, EP 0 004 104 A2, DE 29 10 761 A1, DE 26 21 841 A1, and DE 26 30 798 A1.

Suitable methods for step b) are described, for example, in EP 225 850 A, EP 0 290 387 A, J. Org. Chem. 27 (1962) p. 1695-1703, and U.S. Pat. No. 6,353,107.

Suitable methods for step c) include reaction of (III) with the corresponding epoxide. The reaction is described, for example, in EP0225850 or U.S. Pat. No. 4,001,190.

Suitable methods for step d) include trans-esterification by reaction of (IV) with the carboxylic acid esters, preferably with the methyl esters, or strained esters such as cyclic esters (lactones) where release of ring-strain provides the driving force for the trans-esterification. Preferred catalysts for the trans-esterification are, titanium(IV) isopropoxide, 1,3-diacetoxy-1,1,3,3-tetrabutyldistannoxane, aluminium trichloride, titanium tetrachloride, boron trifluoride, tin tetrachloride, zinc dichloride, aluminium tribromide, tin dichloride, boron trichloride, dibutyltin oxide, aluminium alcoholates, and titanium alcoholates and mixtures thereof.

EXAMPLES

Example 1: 2-[4-(2,2-dimethylpropanoyloxy)-2,2,6,6-tetramethyl-1-piperidyl]ethyl 2,2-dimethylpropanoate (compound 1)

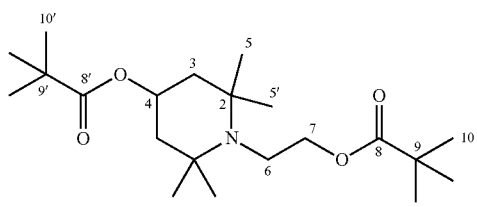 [SMILES: CC(C)(C)C(=O)OCCN1C(C)(C)CC(OC(=O)C(C)(C)C)CC1(C)C]

A three-necked 1 L flask was charged with 53.8 g, (0.27 mol) of 1-(2-Hydroxy-ethyl)-2,2,6,6-tetramethyl-piperidin-4-ol (referred to as "HE-HTMP" in the following) and THF (100 g). The flask was then attached to a rotary evaporator, and 30 ml of THF (and—if present—any water) was distilled off at normal pressure. Then the flask was disconnected from the rotary evaporator, and pyridine (67.0 g, 0.85 mol) was added to the flask.

After cooling to ca. 30° C., a solution of pivalic acid chloride (68.30 g, 0.57 mol) in THF (40 ml) was added within 15 minutes into the cooled (15-20° C.) flask. A viscous suspension was forming during the addition of the acid chloride. After control for complete conversion of the HE-HTMP, water (4.5 ml) was added and the mixture was stirred for another hour in order to decompose the excess pivalic acid chloride. Then the solvent was removed from the reaction mixture on a rotary evaporator, and the residue dissolved in dichloromethane (300 ml). This solution was washed with diluted hydrogen chloride (40 g of a 8% solution), diluted sodium hydroxide (260 g of a 1% solution) and water (250 g). After drying ($Na_2SO_4$), the solvent was removed on the rotary evaporator to leave the crude product as colorless crystalline residue.

This material and the material of a similarly performed batch (from 0.395 mol HE-HTMP) were combined and distilled in vacuum to give 125.8 g of the product (51% yield based on HE-HTMP) as colorless crystals.

bp.=145° C., $9 \cdot 10^{-3}$ mbar
mp.=85° C.
$^1$H-NMR ($CDCl_3$, 400 MHz), δ 1.06, 1.14 (2 s, 6H each, CH3, H-5, H-5'); 1.15, 1.17 (2 s, 9H each, CH3, H-10, H-10'); 1.40 ("tr", 2H, H-3), 1.77 ("dd", 2H, H-3'); 2.63 ("dd", 2H, H-6); 3.91 (m, 2H, H-7); 5.00 ("tr tr", 1H, H-4).
$^{13}$C-NMR (CDCl3, 100 MHz), δ 22.28, 33.60 C-5, C-5'; 27.06, 27.21 C-10, C-10'; 38.55, 38.64 C-9, C-9'; 41.77 C-6; 45.40 C-3; 55.66 C-2; 66.64 C-7; 67.04 C-4; 178.14, 178.52 C-8, C-8'.

Example 2: 3,5,5-Trimethylhexanoic acid 2,2,6,6-tetramethyl-1-[2-(3,5,5-trimethyl-hexanoyloxy)-ethyl]-piperidin-4-yl ester (compound 2)

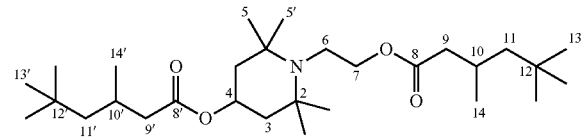

A 250 ml jacketed vessel was fitted with an anchor stirrer, an inner thermometer, a gas inlet tube, a pressure equalized dropping funnel, a Dean-Stark apparatus and a reflux condenser. The outlet from the condenser was connected to a gas absorber in order to trap the hydrogen chloride formed in the reaction.

The flask was checked for air-tightness, and then charged with HE-HTMP (50.3 g, 0.25 mol) and xylene isomer mixture (114.9 g). The reservoir of the Dean-Stark apparatus was filled with xylene isomer mixture, and a slow flow of nitrogen (adjusted to ca. 0.2 L/hour) led through the gas inlet tube into the suspension in the reactor. The mixture was heated at reflux (140° C., mantle temperature 165° C.), and any traces of water were removed via the Dean-Stark apparatus.

Then 3,5,5-trimethyl hexanoyl chloride (86.6 g, 0.49 mol) was added at reflux via the dropping funnel in such a rate that the evolution of the formed hydrogen chloride could be controlled. After complete addition of the acid chloride the initially formed suspension turned into a pale yellow solution which was heated for another hour at reflux and then cooled to 80° C. After washings with water (200 ml), sodium carbonate (twice 50 g of a 10% solution of sodium carbonate in water, twice 100 g of a 5% solution of sodium carbonate in water) the solvent and residual water was removed on the rotary evaporator (initially 100 mbar, 80° C., to finally 0.3 mbar, 80° C.) to leave the product as pale yellow oily liquid (112.0 g, 93% based on HE-HTMP).

NMR: HSQC ($CDCl_3$, RT, 400 MHz) $δ^1H/δ\ ^{13}C$ 1.02, 22.20 (H, C-14); 1.02/22.68, 0.91/22.80 (H, C-5/H, C-5'); 1.96, 27.03/27.07 (H, C-10/H, C-10'); 0.84/30.01, 30.04 C-13, C-13'; 31.05 (C-12, C-12'); 1.09, 33.79 (H, C-5"/H, C-5'"); 2.61, 41.95 (H, C-6); 2.03, 43.99/2.20, 44.28 (H, C-9/H, C-9'); 1.36, 45.71/1.73, 45.74 (H, C-3/H, C-3'); 1.18, 50.52/1.05, 50.54 (H, C-11/H, C-11'); 55.76 (C-2); 3.88, 66.38 (H, C-7); 5.00, 67.06 (H, C-4); 172.58/172.85 (C-8/C-8').

Example 3: 2-Ethyl-hexanoic acid 2-[4-(2-ethyl-hexanoyloxy)-2,2,6,6-tetramethyl-piperidin-1-yl]-ethyl ester (compound 3)

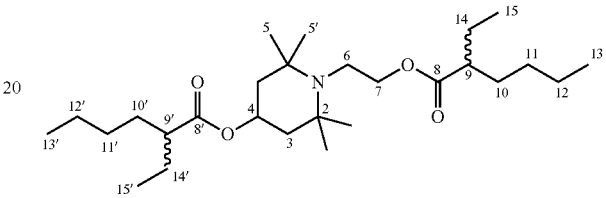

A 250 ml jacketed vessel was fitted with an anchor stirrer, an inner thermometer, a gas inlet tube, a pressure equalized dropping funnel, a Dean-Stark apparatus and a reflux condenser. The outlet from the condenser was connected to a gas absorber in order to trap the hydrogen chloride formed in the reaction.

The flask was checked for air-tightness, and then charged with HE-HTMP (45.0 g, 0.224 mol) and a mixture of xylene isomers (132.4 g). The reservoir of the Dean-Stark apparatus was filled with xylene isomer mixture, and a slow flow of nitrogen (adjusted to ca. 0.2 L/hour) led through the gas inlet tube into the suspension in the reactor. The mixture was heated at reflux (155° C., mantle temperature 165° C.), and ca. 5 ml of xylene was distilled off to remove any residual traces of water. Then 2-ethyl hexanoyl chloride (72.7 g, 0.447 mol) was added at reflux via the dropping funnel in such a rate that the evolution of the formed hydrogen chloride can be controlled. After complete addition of the acid chloride the initially formed suspension turned into a pale yellow solution which was heated for another four hours at reflux and then cooled to 20° C.

The solution was washed with sodium carbonate solution (twice 60 g of a 10% solution of sodium carbonate in water), and water (until the pH of the aqueous layer was neutral and no chloride could be detected in the organic layer; eight times 100 g of water). Checking for chloride was done after the seventh and eighth washing as follows: ca. 0.5 g of the organic layer was dissolved in 10 ml glacial acetic and a few drops of a 5% aqueous solution of silver nitrate added. When the mixture remained clear, the organic phase was considered "chloride free"). Then the organic layer was separated, and the xylene removed on the rotary evaporator (initially 100 mbar, 80° C., to finally 30 mbar, 80° C.). The last traces of xylene were removed in high vacuum (170° C., $10^{-3}$ mbar) to leave the product as yellowish oily liquid (83.2 g, 82% yield based on HE-HTMP).

NMR: HSQC ($CDCl_3$, RT, 400 MHz) $δ^1H, δ\ ^{13}C$ 0.84, 11.73/11.78 (H, C-15/C15'); 0.83, 13.85/13.87 (H, C-13/C-13'); 1.04, 22.09 (H, C-5); 1.24, 22.54 (H, C-12/C12'); 1.44/25.44, 1.54/25.43 (H, C-14/C-14'); 1.20, 29.49/29.59 (H, C-11/C-11'); 1.39/31.70, 1.54,/31.72 (H, C-10/C-10'); 1.11, 33.67 (H, C-5'); 1.37, 1.76/45.64 (H, C-3); 2.62, 41.86 (H, C-6); 2.17, 47.18/47.31 (C-9, C-9'); 55.66 (C-2); 3.92, 66.30 (H, C-7); 5.02, 66.86 (H, C-4); 175.87/176.20 (C-8/C-8').

Example 4: Octadecanoic acid 2-(2,2,6,6-tetramethyl-4-octadecanoyloxy-piperidin-1-yl)-ethyl ester (compound 4)

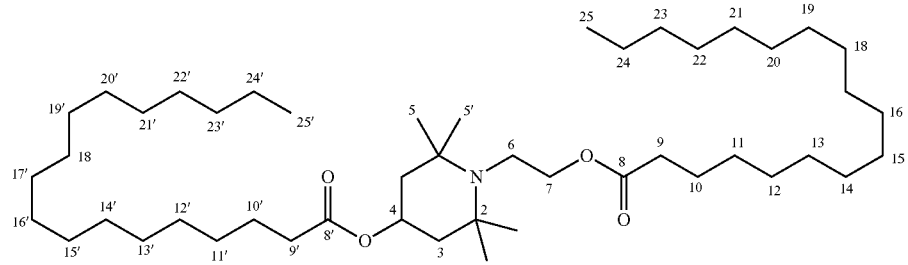 [SMILES: CCCCCCCCCCCCCCCCCC(=O)OCCN1C(C)(C)CC(OC(=O)CCCCCCCCCCCCCCCCC)CC1(C)C]

A jacketed 1.5 L flask was fitted with an anchor stirrer, an inner thermometer and a Dean-Stark apparatus with reflux condenser. This flask was charged with xylene (435 g, mixture of isomers) and HE-HTMP (100.6 g, 0.5 mol). The mixture was heated at reflux to remove azeotropically any present water via the Dean-Stark apparatus. Then the temperature was reduced to 100° C., and methyl stearate (316.5 g, 1.03 mol) and tetrabutyl orthotitanate (0.102 g, 0.3 mmol) were added. The mixture was heated at reflux for totally 8 hours (interrupted by 60 h) and then transferred warm into a flask. The solvent was removed on a rotary evaporator, and the remaining melt of the product poured into methanol (ca. 1 L). After standing over night at ambient temperature the crystallized product was filtered off and washed with methanol (ca. 400 ml). After drying colorless crystals (218.6 g, 59.5%) were obtained.

$^{13}$C-NMR (APT, CDCl$_3$, 100 MHz, RT) δ 14.07 (C-25, C-25'); 22.13 (C-5); 22.65 (C-24, C-24'); 24.92, 24.97 (C-10, C-10'); 26.09, 29.14, 29.24 (2 C), 29.33 (2 C), 29.43, 29.44, 29.58 (2 C), 29.62 (2 C), 29.63 (2 C), 29.65 (2 C), 29.66-29.68 (8 C), (C10-C22, C-10'-C22'); 31.90 (C-23, C-23'), 33.70 (C-5'), 34.21, 34.61 (C-9, C-9'); 41.89 (C-6); 45.62 (C3); 55.73 (C-2); 66.45 (C-7); 67.10 (C-4), 173.41, 173.68 (C-8, C-8').

Example 5: Hexadecanoic acid 2-(4-hexadecanoyloxy-2,2,6,6-tetramethyl-piperidin-1-yl)-ethyl ester (compound 5)

A 250 ml jacketed vessel was fitted with an anchor stirrer, an inner thermometer, a gas inlet tube, a pressure equalized dropping funnel, a Dean-Stark apparatus and a reflux condenser.

The flask was charged with HE-HTMP (16.1 g, 80 mmol), Petrol (80 g), ("Petrol" is an aryl free mixture of alkanes with a boiling range from 150-190° C.), and methyl palmitate (42.6 g, 158 mmol). The Dean-Stark apparatus was filled with Petrol (30 g), and then the mixture was heated at reflux (mantle temperature 190° C.) and ca. 30 ml of petrol was distilled off to remove any residual traces of water. Then the mixture was cooled to 100° C., and aluminium triisopropylate (0.32 g, 1.57 mmol, 1 mol %) was added. The mixture was again heated at reflux (mantle temperature 190° C.), and kept stirring for seven hours. Then, a light vacuum was applied to remove the last traces of the formed methanol, and finally the mixture was cooled to ambient temperature. The cooled mixture was dissolved in ethanol (250 ml) and bleached with a bleaching earth for about ten minutes at reflux. After removal of the bleaching earth by filtration, the product crystallized from the filtrate and was filtered off, washed with methanol (ca. 25 g) and dried to give the product (23.0 g, 44%) as colourless crystals.

The product is prepared more efficiently as follows: A 250 mil jacketed vessel was fitted with an anchor stirrer, an inner thermometer and a descending condenser was charged with HE-HTMP (50.1 g, 0.249 mol) and methyl palmitate (134.3 g, 0.497 mol). This mixture was heated at 151° C., and then tetrabutyl orthotitanate (0.14 g, 0.4 mmol) was added. The mixture was kept at 151° C. for 24 hours (GC conversion ca. 99%) and then cooled to 80° C. The contents of the reactor were then added into refluxing methanol (300 g). The obtained emulsion was allowed to cool slowly and seeded when the temperature was at 35° C. A suspension of seed crystals was obtained by taking ca. 1 ml of the emulsion into a test tube and scratching with a spatula. After cooling to ambient temperature and stirring for another couple of hours the crystallised product was filtered off, washed with methanol (ca. 100 ml) and dried on the rotavapor (30° C., 6 hours) to give 158.4 g of colorless crystals (94.1% of theory).

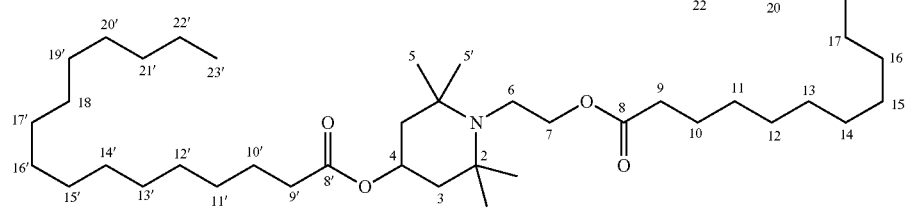

¹H-NMR (CDCl₃, 400 MHz, RT) δ 0.88, 0.89 (t, 3H each, H-23, H-23'); 1.10, 1.17 (s, 6H each, H-5, H-5'); 1.27 (m, 48H, H-11 to H-22, H11' to H-22'); 1.43, 1.83 (t, dd, 2H each, H-3, H-3'); 1.63 (dq, 2H each, H-11, H-11'); 2.28 (q, 4H, H-9, H-9'); 2.69 (t, 2H, H-6); 3.97 (t, 2H, H-7); 5.08 (m, 1H, H-4)

13C-NMR (CDCl₃, 100 MHz, RT,) δ 14.11 C23, C-23'; 22.17, 33.74 C-5, C-5'; 22.69 C22, C-22'; 24.96, 25.01 C-10, C-10'; 29.12-29.69 C-11 to C-22, C-11' to C-22'; 31.93 C21, C-21'; 34.27, 34.67 C-9, C-9'; 41.91 C-6; 45.64 C-3; 55.77 C-2; 66.49 C-7; 67.17 C-4.

Example 6: Tetradecanoic acid 2-(2,2,6,6-tetramethyl-4-tetradecanoyloxy-piperidin-1-yl)-ethyl ester (compound 6)

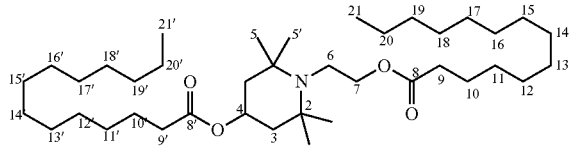

A jacketed 250 ml flask was fitted with an anchor stirrer, inner thermometer, gas inlet tube and a Dean-Stark apparatus with reflux condenser. The flask was charged with HE-HTMP (17.1 g, 84 mmol), Petrol (80 g), ("Petrol" is defined above), and methyl laurate (42.4 g, 171 mmol). The mixture was heated at reflux (mantle temperature 200° C.), and any residual water was removed via the Dean-Stark apparatus. Then the temperature was reduced (mantle temperature 80° C.), and aluminium tri-isopropylate (0.37 g, 1.8 mmol) was added. Then the mixture was again heated at reflux (mantle temperature=190° C.) for four hours and then the solvent was removed at slightly reduced pressure (800 mbar) within four hours. The remaining molten product (57.4 g) was a brownish oily liquid which solidified on standing, mp.=42–44° C.

The product can be prepared also as follows: A 250 ml jacketed vessel was fitted with an anchor stirrer, an inner thermometer and a descending condenser was charged with HE-HTMP (30.6 g, 0.15 mol) and methyl tetradecanoate (80.9 g, 0.33 mol). This mixture was heated and at an inner temperature of 143° C. tetrabutyl orthotitanate (0.178 g, 0.052 mmol) was added. The mantel temperature was set to 180° C. and mixture was kept stirring for 23 hours, when the inner temperature had reached 148° C. A GC-sample showed ca. 94% conversion. Thus, the mixture was cooled to 80° C. and then added into refluxing methanol (300 g). The obtained emulsion was allowed to cool slowly and seeded when the temperature was at 35° C. A suspension of seed crystals was obtained by taking ca. 1 ml of the emulsion into a test tube and scratching with a spatula. After cooling to ambient temperature and stirring for another couple of hours the crystallized product was filtered off, washed with methanol (ca. 100 ml) and dried on the rotavapor (30° C., 23 mbar, 4 hours) to give 89.8 g (96.2% based on HE-HTMP) of colorless crystals ¹H-NMR (CDCl₃, 400 MHz, RT) δ 0.89 (t; 6H, H-12, H-12'); 1.10, 1.16 (s, 12H, H-5, H-5'); 1.27 (m, 40H, H-11 to H-20, H-11' to H-20'); 1.43 (t, 2H, H-3); 1.62 (q, 4H, H-10, H-10'); 1.82 (dd, 2H, H-3); 2.27, 2.29 (2 t, 2H each, H-9, H-9'); 2.69 (t, 2H, H-6); 3.97 (t, 2H, H-7); 5.08 (tr tr, 1H, H-4).

¹³C-NMR (CDCl₃, 100 MHz, RT) δ 14.24, C-21, C-21; 22.30 C-5, 22.82, C-20, C-20'; 25.09, 25.13 C-10, C-10'; 29.24, 29.29, 29.40, 29.48, 29.59, 29.73, 29.78, 29.80 C-11 to C-18, C11' to C-18'; 32.05 C-19, C-19'; 33.87 C-5'; 34.39, 34.79 C-9, C-9'; 42.04 C-6; 45.78 C-3; 55.90 C-2; 66.62 C-7; 67.28 C-4; 173.62, 173.89 C-21, C-21'.

Example 7: Dodecanoic acid 2-(4-dodecanoyloxy-2,2,6,6-tetramethyl-piperidin-1-yl)-ethyl ester (compound 7)

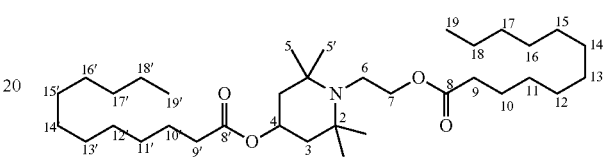

A jacketed 250 ml flask was fitted with an anchor stirrer, inner thermometer, and a Dean-Stark apparatus with reflux condenser. The flask was charged with HE-HTMP (17.1 g, 84 mmol), "Petrol" (78.6 g), ("Petrol" is defined above), methyl laurate (38.4 g, 176 mmol) and aluminium tri-isopropylate (0.4 g, 1.96 mmol). The obtained mixture was heated at reflux (mantle temperature 190° C.) for four hours. A slight vacuum (800 mbar) was applied and heating was continued for another 5 hours. The conversion was 95% as determined by NMR after removal of the solvent in vacuum (136° C., 0.19 mbar) the product was obtained as yellow oil (50.9 g, 102%), which crystallized slowly at ambient temperature.

The product can be prepared also as follows: A 250 ml jacketed vessel was fitted with an anchor stirrer, an inner thermometer and a descending condenser was charged with HE-HTMP (38.41 g, 0.191 mol) and methyl laurate (86.01 g, 0.40 mol). This mixture was heated and at an inner temperature of 151° C. tetrabutyl orthotitanate (0.16 g, 0.47 mmol) was added. The mantel temperature was set to 180° C. and mixture was kept stirring for 24 hours. A GC-sample showed ca. 99% conversion. Thus, the mixture was cooled to 80° C. and then added into refluxing methanol (300 g). The obtained emulsion was allowed to cool slowly and seeded when the temperature was at 35° C. A suspension of seed crystals was obtained by taking ca. 1 ml of the emulsion into a test tube and scratching with a spatula. After cooling to ambient temperature and stirring for another couple of hours the crystallised product was filtered off, washed with methanol (ca. 100 ml) and dried on the rotavapor (30° C., 23 mbar, 6 hours) to give 98.4 g (91.1% based on HE-HTMP) of colorless crystals ¹H-NMR (CDCl₃. 400 MHz, RT) δ 0.89 (tr, 6H, H-19, H-19'); 1.10, 1.16 (2 s, 6H each, H-5, H-5'); 1.20-1.38 (br m, 32H, H-11-H-18, H-11'-H-18'); 1.43 ("tr", 2H, H-3); 1.62 (m, 4H, H-10, H-10'); 1.83 ("dd", 2H, H-3'); 2.28 (m, 4H, H-9, H-9'); 2.68 ("tr", 2H, H6); 3.97 ("tr", 2H, H-7); 5.08 (tr tr, 1H, H-4).

¹³C-NMR (CDCl₃, 100 MHz, RT) δ 14.10 (2 C, C-19, C-19'); 22.16 (2 C, C-5); 22.67 (2 C, C-18, C-18'); 24.95, 25.00 (2 C, C-10, C-10'); 29.10 (1 C), 29.16 (1 C), 29.26 (2 C), 29.32 (2 C), 29.44 (1 C), 29.45 (1 C), 29.59 (4 C) C-11-C16, C-11'-C-16'; 31.90 (2 C, C-17, C-17'); 33.73 2 C

C-5'; 34.26, 34.65 (C-9, C-9'); 41.90 (C-6); 45.64 (C-3); 55.76 (C-2); 64.48 (C-7); 67.15 (C-4); 173.50, 173.76 (C-8, C-8').

Example 8: Hexanoic acid 2-(4-hexanoyloxy-2,2,6,6-tetramethyl-piperidin-1-yl)-ethyl ester (compound 8)

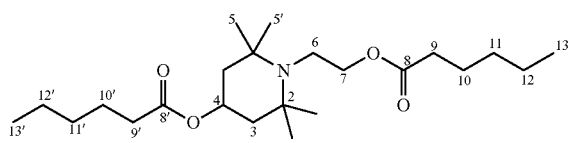 [SMILES: CCCCCC(=O)OCCN1C(C)(C)CC(OC(=O)CCCCC)CC1(C)C]

A jacketed 250 ml flask was fitted with an anchor stirrer, inner thermometer, and a reflux condenser which was connected to a gas absorber. Into this flask was charged HE-HTMP (50.14 g, 0.249 mol) and xylene (isomer mixture, 120 g). The mixture was heated at reflux, and then at an inner temperature of 1420° C. was added hexanoic acid chloride (67.77 g 0.503 mol) within one hour. Shortly after the beginning of the addition of the acid chloride the reaction mixture turned into a viscous suspension which later became rather liquid again. After the complete addition of the acid chloride the mixture was kept at 142° C. for another two hours and then cooled to 80° C. The mixture was then washed twice with a solution of sodium carbonate (each 50 g of a 10% solution) and water (40 g). After removal of the xylenes on the rotavapor the product was distilled in vacuum (b.p. 190-200° C. at 0.001 mbar) to give 81.5 g (82.3% yield) of the product as colourless oil.

$^1$H-NMR (CDCl$_3$, 400 MHz, RT) δ 0.89 (t, 3H each, H-13, H-13'); 1.08, 1.15 (s, 6H each, H-5, H-5'); 1.32 (m, 8H, H-11-H-12, H11'-H12'); 1.41, 1.80 (t, q; 2H each, H3, H-3'); 1.61 (q, 2H each, H-10, H-10'); 2.27 (q, 4H, H-9, H-9'); 2.67 (t, 2H, H-6); 3.95 (t, 2H, H-7); 5.06 (m, 1H, H-4).
$^{13}$C-NMR (CDCl$_3$, 100 MHz, RT) δ 13.88 C-13, C-13'; 22.15, 33.72 C-5, C-5'; 22.30 C-12, C-12'; 24.61, 24.65 C-10, C-10'; 31.26, 31.61 C-11, C-11'; 34.19, 34.58 C-9, C9'; 41.89 C-6; 45.62 C-3; 55.75 C-2; 66.47 C-7; 67.14 C-4; 173.45, 173.73 C-8, C-8'

Example 9: Propionic acid 2-(2,2,6,6-tetramethyl-4-propionyloxy-piperidin-1-yl)-ethyl ester (compound 9)

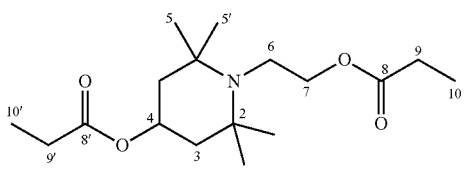 [SMILES: CCC(=O)OCCN1C(C)(C)CC(OC(=O)CC)CC1(C)C]

A three necked flask with magnetic stirrer, reflux condenser, and pressure equalized dropping funnel was charged with HE-HTMP (100.0 g, 0.497 mol). The apparatus was flushed thoroughly with nitrogen, and then immersed in an oil bath of 140° C. Then propionic acid anhydride (131.4 g, 1.011 mol) was added via the dropping funnel within 75 minutes. During the addition of the propionic anhydride, the reaction mixture liquefied, after the addition of the propionic anhydride was complete, the mixture was heated at 150° C. for 90 minutes (after 90 minutes gas chromatography indicated completion of the reaction).

The propionic acid was removed from the reaction mixture on a rotary evaporator, and the residue poured into a beaker containing water (ca. 250 ml) and dichloromethane (ca. 300 ml). The pH of the bi-phasic mixture was carefully adjusted with sodium hydrogen carbonate to pH=7.0, and then the organic layer separated with a separatory funnel, dried (sodium sulphate) and distilled in vacuum. The product (144.1 g, 92.6% yield) was obtained as pale yellow oil (bp 120-141° C., 5·10$^{-3}$–7·10$^{-3}$ mbar), which solidified on standing.

mp.≈25° C.

$^1$H-NMR (CDCl$_3$, 400 MHz, RT) δ 0.98, 1.05 (2 s, 6H each, H-5, H-5'); 1.01, 1.03 (2 tr, 3H each, J=7.5 Hz, H-10, H-10'); 1.31 ("tr", 2H), 1.71 ("dd", 2H) H-3, H3'; 2.18, 2.21 (2 q, 2H each, H-9, H-9'); 2.58 (tr, 2H, H-6); 2.58 (tr, 2H, H-7); 4.96 (tr tr, J=11.6 Hz, J=4.1 Hz, 1H, H-4). $^{13}$C-NMR (CDCl$_3$, 100 MHz, RT) δ 8.96, 8.97 C-10, C-10'; 27.28, 27.70 C-5, C-5'; 41.79 C-6; 45.54 C-3; 55.63 C-2; 66.36 C-7; 67.02 C-4; 173.76, 174.05 C-8, C-8'.

Example 10: Acetic acid 2-(4-acetoxy-2,2,6,6 tetramethyl-piperidin-1-yl)-ethyl ester (compound 10)

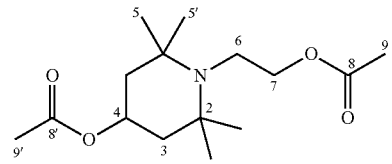 [SMILES: CC(=O)OCCN1C(C)(C)CC(OC(C)=O)CC1(C)C]

A three necked flask with over-head stirrer, reflux condenser, pressure equalized dropping funnel was charged with HE-HTMP (101.0 g, 0.502 mol). The apparatus was flushed thoroughly with nitrogen, and then immersed in an oil bath of 130° C. Then acetic acid anhydride (103.2 g, 1.011 mol) was added via the dropping funnel within ca. one hour. During the addition of the acid anhydride, the reaction mixture liquefied. Four hours after the addition of the acetic anhydride was completed, the conversion of the HE-HTMP was 93%, as indicated by gas chromatography. After another 90 minutes at 130° C., the reaction mixture was allowed to cool to ambient temperature, diluted with dichloromethane (ca. 200 ml) and poured into water. The pH of the bi-phasic mixture was carefully adjusted with sodium hydrogen carbonate to pH=7.0. The organic layer was then separated with a separatory funnel, and washed twice with water (ca. 200 ml each), dried (sodium sulphate) and the solvent removed on a rotary evaporator. The residue (141 g reddish oil) was distilled in vacuum (bp.=115°-125° C. at 0.01-0.019 mbar) to give a yellowish oil (129.5 g, 90.4% yield) which solidified on standing.

mp.=53-54° C.

$^1$H-NMR (CDCl$_3$, 400 MHz, RT) δ 1.08, 1.15 (2 s, 6H each, H-5, H-5'); 1.41 ("tr", 2H), 1.82 ("dd", 2H), H-3, H-3'; 2.02, 2.04 (2 s, 3H each, H-9, H-9'); 2.68 (tr, 2H, H-6); 3.96 (tr, 2H, H-7); 5.06 (tr tr, 1H, H-4).
$^{13}$C-NMR (CDCl$_3$, 100 MHz) δ 20.92, 21.40 C-9, C-9'; 22.14, 33.72 C-5, C-5'; 41.85 C-6; 45.60 C-3; 55.60 C-2; 66.64 C-7; 67.40 C-4; 170.61, 171.89 C-8, C-8'.

Example 11: 3-Methoxy-propionic acid 2-[4-(3-methoxy-propionyl-oxy)-2,2,6,6-tetra-methyl-piperidin-1-yl]-ethyl ester (compound 11)

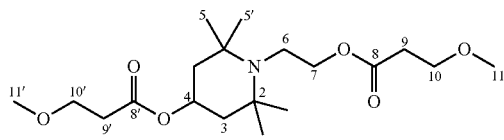

A jacketed 250 ml flask was fitted with an anchor stirrer, inner thermometer, gas inlet tube and a Dean-Stark apparatus with reflux condenser. The flask was charged with HE-HTMP (138 g, 0.69 mol) and xylenes (108 g, mixture of isomers). The mixture was heated at reflux (mantle temperature=150° C.), and ca. 40 ml of the solvent was distilled off in order to remove the water as azeotrope with the xylenes. Then the temperature was reduced to 80° C., and 3-methoxypropionic acid methyl ester (92.0 g, 0.75 mol) and tetrabutyl ortho-titanate (0.1 g) were added. The mixture was then heated again at reflux, and the forming methanol distilled off. After completion of the reaction the mixture was allowed to cool, and the resulting solution of the product was washed three times with water (250 ml each time). After drying (sodium sulphate) and removal of the xylenes on the rotary evaporator the residue was distilled in vacuum (boiling point 167° C./1.1*10$^{-2}$ mbar) to give the product as clear, pale yellow liquid.

$^1$H-NMR (CDCl$_3$, 400 MHz) δ 1.08, 1.15 (2 s, 6H each, H-5, H-5'); 1.43 ("tr", 2H), 1.83 ("d d", 2H) H-3, H-3'; 2.53, 2.56 (2 tr, 2H each, H-9, H-9'); 2.69 ("dd", 2H, H-6); 3.34, 3.35 (2 s, 3H each, H-11, H-11'); 3.64, 3.65 (2 tr, 2H each, H10, H-10'); 3.98 ("dd", 2H, H-7); 5.10 (tr tr, 1H, H-4).

$^{13}$C-NMR (CDCl$_3$, 100 MHz) δ 22.09, 33.63 C-5, C-5'; 34.83, 35.18 C-9, C-9'; 41.75, C-6; 45.49, C-3; 55.70, C-2; 58.63, 58.65 C-11, C-11'; 66.64 C-7; 67.53 C-4; 67.86, 67.88 C-10, C-10'; 171.04, 171.34 C-8, C-8'.

Example 12: Methoxy-acetic acid 2-[4-(2-methoxy-acetoxy)-2,2,6,6-tetramethyl-piperidin-1-yl]-ethyl ester (compound 12)

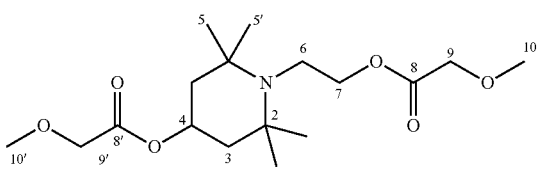

This compound was prepared in an analogous manner as described in Example 11 using 2-methoxyacetic acid methyl ester instead of 3-methoxypropionic acid methyl ester. The crude products from two batches (in one batch 0.2 mol HE-HTMP were used, in the other batch 0.4 mol HE-HTMP were used, both crude products were brown oils) were combined for purification. The combined crude materials were dissolved in toluene (250 ml), and the dark brown solution de-colorized with bleaching earth (75 g and 50 g of Tonsil Optimum FF, Clariant). After filtration, the solvent was removed from the obtained light brown solution on the rotary evaporator. On cooling to ambient temperature the product started to crystallize. Thus, the material was re-dissolved in a minimum quantity of toluene at reflux (ca. 100 ml) and the solution allowed to cool slowly to 0° C. Then n-hexane (170 g) was added to bring crystallization to completion. The obtained almost colorless crystals were filtered off, washed with little n-hexane and dried to give 115.9 g (62% combined yield based on HE-HTMP) of almost colorless crystals.

mp.=57-58° C.

$^1$H-NMR (CDCl$_3$, 400 MHz) δ 0.80, 0.86 (2 s, 6H each, H-5, H-5'); 1.15 "tr", 2H, 1.55 "dd", 2H, H-3, H-3'; 2.41 ("dd", 2H, H-6); 3.11, 3.17 (2 s, 3H each, H-10, H-10'); 3.67, 3.71 (2 s, 3H each, H-9, H-9'); 3.73, "dd", 2H, H-7); 4.83 (tr tr, 1H, H-4).

$^{13}$C-NMR (CDCl3, 100 MHz) δ 21.91, 33.35 C-5, C-5'; 41.51 C-6; 45.29 C-3; 55.49 C-2; 58.78 58.83 C-10, C-10'; 66.28 C-7; 67.56 C-4; 69.33, 69.52 C-9, C-9'; 169.38, 169.68 C-8, C-8'.

Example 13: 4-Oxo-hexanoic acid 2,2,6,6-tetramethyl-1-[2-(4-oxo-pentanoyloxy)-ethyl]-piperidin-4-yl ester (compound 13)

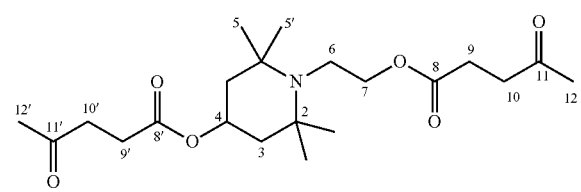 [SMILES: CC(=O)CCC(=O)OCCN1C(C)(C)CC(OC(=O)CCC(C)=O)CC1(C)C]

A 250 ml jacketed vessel was fitted with an anchor stirrer, an inner thermometer and a descending condenser. It was charged with HE-HTMP (84.5 g, 0.42 mol) and methyl laevulinate (114.76 g, 0.882 mol). This mixture was heated and at an inner temperature of 151° C. tetrabutyl orthotitanate (0.12 g, 0.36 mmol) was added. The mantel temperature was set to 180° C. and mixture was kept stirring for 24 hours. Then the excess methyl laevulinate was removed in vacuum (1 h at 3 mbar), and then cooled to 80° C. The product was obtained as a very viscous brown oil, 154.4 g (92.5% based on HE-HTMP).

$^1$H-NMR (CDCl$_3$, 400 MHz, RT) δ 0.89, 0.96 (2 s, 6H each, H-5, H-5'); 1.24, 1.63 (2 m, 2H each, H-3, H-3'); 2.00 (s, 6H, H-12, H-12'); 2.36 (tr, 4H, H-9, H-9'); 2.49 (tr, 2H, H-6); 2.56 ("tr", 4H, H-10, H-10'); 3.77 (tr, 2H; H-7); 4.86 (trtr, 1H, H-4).

$^{13}$C-NMR (CDCl$_3$, 100 MHz, RT,) δ 21.87, 33.41 (C-5, C-5'); 27.57, 28.03 (C-9, C-9'); 29.50, 29.52 (C-12, C-12'); 37.56, 37.59 (C-10, C-10'); 41.51 (C-6); 45.24 (C-3); 55.45 (C-2); 66.42 (C-7); 67.34 (C-4); 171.89, 172.25 (C-8, C-8'); 206.10; 206.17 (C-11, C11').

Application Examples

Coating Formulations A: (Acid Catalyzed High Solid Clear Coating Formulation)

| | Weight-% |
|---|---|
| Joncryl ® 510 (80% in n-butyl acetate) (SGO acrylic resin, BASF SE) | 56.2 |

-continued

|  | Weight-% |
|---|---|
| Luwipal ® 066 (95%) (hexamethoxymethyl melamine resin, BASF SE) | 19.2 |
| n-butanol (solvent) | 24.0 |
| Dow Corning ® 57 (10% in n-butanol) (slip and leveling agent) | 0.6 |
|  | 100.0 |
| Hardener (catalyst): |  |
| p-toluenesulfonic acid (40% in n-butanol) | 2.0 |

The formulations A were stabilized with 3.1 wt % (based on resin solids) Tinuvin® 384-2 (UV absorber, BASF SE).

Each coating formulation A further contained 1.6 wt % (based on resin solids) of one of compounds 1 to 13, or of Tinuvin 622, or of Tinuvin 123.

The clear coat formulations were subsequently sprayed onto a silver metallic base coat (DFT base coat: 18 μm) in a thickness resulting after cure (130° C., 30') in a dry film thickness of 40 μm.

Coating Formulations B: (Epoxy Carboxy Coating Formulation: Ultra Gloss F 3000 (BASF Coatings, Japan))

Component A/component B (50/50) [A=backbone, B=hardener component]

The formulations B were stabilized with 2 wt. % (based on resin solids) Tinuvin 384-2. Each coating formulation B further contained 1 weight-% (based on resin solids) of one of compound 1 to 13, or of Tinuvin 622, or of Tinuvin 123.

Solid content component A plus B: 57%

The clear coat formulations were subsequently sprayed onto a silver metallic base coat (DFT base coat: 18 μm) in a thickness resulting after cure (140° C., 30') in a dry film thickness of 40 μm.

Coating Formulations C: (Thermo-Setting Acrylic Melamine Clear Coating Formulation)

|  | Weight-% |
|---|---|
| Viacryl ® SC 303 (60% in xylene/butanol; 26/9) (acrylic resin, Cytec) | 30.2 |
| Viacryl ® SC 370 (75% in SN/butylacetate) (acrylic resin, Cytec) | 25.6 |
| Maprenal ® MF 650 (55% in isobutanol) (isobutylated melamine-formaldehyde resin, Ineos) | 29.9 |
| Butyl acetate/butanol (37:8) (solvent) | 4.7 |
| Isobutanol (solvent) | 5.3 |
| Solvesso ® 150 (solvent, Exxon Mobil Chemicals) | 3.0 |
| Baysilone ® MA (1% in Solvesso 150) (leveling agent, Momentive) | 1.3 |
|  | 100.0 |

Solids content: 53%

The formulations C were stabilized with 2 wt. % (based on resin solids) Tinuvin® 384-2 (UV absorber, BASF SE).

Each coating formulation C further contained 1 weight-% (based on resin solids) of one of compound 1 to 13, or of Tinuvin 622, or of Tinuvin 123.

The clear coat formulations were subsequently sprayed onto a silver metallic base coat (DFT base coat: 18 μm) in a thickness resulting after cure (130° C., 30') in a dry film thickness of 40 μm.

Coating Formulations D: (Long Oil Alkyd Clear Wood Coating Formulation)

|  | Weight-% |
|---|---|
| Worleekyd B 870, 75% Exxsol D40 (long oil alkyd, Worlee-Chemie GmbH) | 45.70 |
| Octa-Soligen Calcium 5 (metal drier, OMG Borchers) | 2.75 |
| Octa-Soligen Zirconium 12 (metal drier, OMG Borchers) | 0.30 |
| Octa-Soligen Cobalt 10 (metal drier, OMG Borchers) | 0.35 |
| Exkin 2 (anti-skinning agent, Elementis) | 0.20 |
| Exxsol D30 (solvent, ExxonMobil Chemicals) | 50.00 |
| Tinuvin ® 99-2 (UV absorber, BASF SE) | 0.70 |
|  | 100.00 |

Solids content: 34%

Each coating formulation D further contained 1 wt. % (based on resin solids) of one of compounds 1 to 13, of Tinuvin 622, or of Tinuvin 123.

The clear coat formulations were subsequently applied by brush (thickness: 3 layers a 80 g/m² resulting after drying at room temperature in a dry film thickness of 70 μm).

Solubility Tests

The solubility of above described coating formulations A, B, C, and D (each containing one of compounds 1 to 13, of Tinuvin 622, or of Tinuvin 123 in the amounts given above), was tested. The solubility was assessed qualitatively by visual aspect of turbidity of the solution and residual not dissolved particles in the solution. Results are given in the following table:

| Compound | Formulations A | Formulations B | Formulations C | Formulations D |
|---|---|---|---|---|
| Tinuvin 622 | not soluble | not soluble | not soluble | not soluble |
| Tinuvin 123 | soluble | soluble | soluble | Soluble |
| Compound 1 | soluble | slow dissolution | soluble | Soluble |
| Compound 2 | soluble | soluble | soluble | soluble |
| Compound 3 | soluble | soluble | soluble | soluble |
| Compound 4 | slow dissolution | not soluble | soluble | soluble |
| Compound 5 | Not soluble | Not soluble | slow dissolution | slow dissolution |
| Compound 6 | Not soluble | Not soluble | slow dissolution | soluble |
| Compound 7 | Soluble | soluble | slow dissolution | soluble |
| Compound 8 | Soluble | soluble | slow dissolution | soluble |
| Compound 9 | soluble | soluble | soluble | soluble |
| Compound 10 | soluble | soluble | soluble | slow dissolution |
| Compound 11 | soluble | soluble | soluble | soluble |
| Compound 12 | soluble | soluble | soluble | soluble |
| Compound 13 | soluble | soluble | soluble | soluble |

Compatibility Tests:

For assessment of the compatibility (exudation due to incompatibility in the coating) the gloss of coatings B was measured after curing (BYK Haze-Gloss device 4601).

| Compound | gloss (20°) |
|---|---|
| Tinuvin 123 | 81 |
| Compound 1 | 87 |
| Compound 2 | 87 |
| Compound 3 | 89 |
| Compound 7 | 90 |
| Compound 9 | 88 |
| Compound 10 | 88 |
| Compound 11 | 88 |
| Compound 12 | 88 |
| Compound 13 | 88 |

The compounds do not indicate any negative effect on compatibility in the cured coating like gloss loss.

Accelerated Weathering Tests:

Coatings A, B, C, and D, as given in the tables below were tested under artificial weathering cycles to evaluate the stabilization, as indicated by the gloss retained after a given time of the artificial weathering cycle and crack formation.

Coatings A, Xenon Lamps (SAE J 1960):

| Compound | gloss (20°) after 3000 hours |
|---|---|
| Without HALS | 77 |
| Tinuvin 123 | 90 |
| Example 1 | 90 |
| Example 2 | 90 |
| Example 3 | 90 |
| Example 4 | <80 |
| Example 7 | 91 |
| Example 8 | 91 |
| Example 9 | 90 |
| Example 10 | 92 |
| Example 11 | 92 |
| Example 12 | 89 |
| Example 13 | 95 |

Coatings B, Xenon Lamps (SAE J 1960):

| Compound | Gloss (20°) after 3500 hours | Gloss (20°) after 4500 hours |
|---|---|---|
| Without HALS | 77*) | — |
| Tinuvin 123 | 87 | 87 |
| Example 1 | 85 | 79 |
| Example 2 | 87 | 87 |
| Example 3 | 90 | 83 |
| Example 7 | 88 | 84 |
| Example 9 | 84 | 77 |
| Example 10 | 84 | 70*) |
| Example 11 | 88 | 87 |
| Example 12 | 88 | 86 |
| Example 13 | 88 | 84 |

*)cracking

Coatings B, UVB-313 nm Lamps (Q-UV DIN EN ISO 4292-3):

| Compound | Gloss (20°) after 3000 hours | Gloss (20°) after 3500 hours |
|---|---|---|
| Without HALS | 61*) | — |
| Tinuvin 123 | 89 | 82 |
| Example 1 | 71 | —*) |
| Example 2 | 89 | 88 |
| Example 3 | 87 | 76 |
| Example 7 | 89 | 86 |
| Example 9 | 76*) | — |
| Example 10 | 70*) | — |
| Example 11 | 78 | 72 |
| Example 12 | 74 | 65 |
| Example 13 | 83 | 80 |

*)cracking

Coatings C, Xenon Lamps (SAE J 1960):

| Compound | Gloss (20°) after 4000 hours |
|---|---|
| Without HALS | 73 |
| Tinuvin 123 | 93 |
| Example 1 | 93 |
| Example 2 | 91 |
| Example 3 | 89 |
| Example 9 | 87 |
| Example 10 | 84 |
| Example 11 | 92 |
| Example 12 | 91 |
| Example 13 | 93 |

Coatings C, UVB-313 nm Lamps (Q-UV DIN EN ISO 4292-3):

| Compound | Gloss (20°) after 3000 hours | Gloss (20°) after 3500 hours |
|---|---|---|
| Without HALS | <5 | |
| Tinuvin 123 | 86 | 85 |
| Example 1 | 74 | <35 |
| Example 2 | 85 | 81 |
| Example 3 | 85 | 83 |
| Example 9 | 83 | 64*) |
| Example 10 | 13 | — |
| Example 11 | 81 | 54 |
| Example 12 | 12 | — |
| Example 13 | 87 | 77 |

*)cracking

Coatings D, UV-A 340 nm Fluorescence Bulbs (EN 927-6), Formulation D:

| Compound | Extent of delamination/degradation after 1250 hours |
|---|---|
| Without HALS | Severe |
| Tinuvin 123 | Slight to moderate |
| Example 2 | slight |
| Example 10 | Moderate |
| Example 12 | Slight to moderate |

The compounds are suitable for stabilizing different types of coatings by retaining gloss and preventing from cracking, degradation or delamination.

The following examples illustrate the invention further. All percentages and parts are by weight, unless stated otherwise. Compound 2 (3,5,5-trimethylhexanoic acid 2,2, 6,6-tetramethyl-1-[2-(3,5,5-trimethyl-hexanoyloxy)-ethyl]-piperidin-4-yl ester) corresponds to the formula

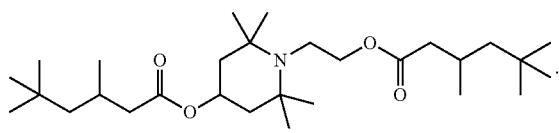 [SMILES: CC(CC(=O)OCCN1C(C)(C)CC(OC(=O)CC(C)CC(C)(C)C)CC1(C)C)CC(C)(C)C]

Example A-1: Stabilization of a Polymethylmethacrylate (PMMA) Solution Cast Film (1)

10 g of Plexiglas 7 N are dissolved in 40 g methylene chloride together with 50 mg of compound 2. Films are drawn with the help of an automatic blade (Erichsen®) with a blade speed of 12 mm/sec and a gap height of 120 μm. The films are then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table A-1.

TABLE A-1

| | hours | | | | |
|---|---|---|---|---|---|
| | 0 | 99 | 263 | 472 | 1006 |
| YI (Yellowness Index)*) | −0.5 | 0.5 | 0.3 | 0.3 | 0.5 |
| ΔE (Color difference)*) | 0.0 | 1.0 | 0.8 | 0.9 | 1.1 |
| b* (Color coordinate)*) | −0.2 | 0.4 | 0.3 | 0.3 | 0.4 |

*)Low values are desired.

Example A-2: Stabilization of a Polymethylmethacrylate (PMMA) Solution Cast Film (2)

10 g of Plexiglas 7 N are dissolved in 40 g methylene chloride together with 50 mg of compound 2 and 100 mg of 2,2'-methylenebis(6-(2H-benzotriazol-2-yl)-4-1,1,3,3-tetramethylbutyl)phenol (Tinuvin®360). Films are drawn with the help of an automatic blade (Erichsen®) with a blade speed of 12 mm/sec and a gap height of 120 μm. The freshly drawn film is dried for 10 minutes. The resulting film with a thickness of 25 μm has a yellowness index of 16.3. (DIN 6167(1980-01)). This film is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table A-2.

TABLE A-2

| | hours | | | | |
|---|---|---|---|---|---|
| | 0 | 99 | 263 | 472 | 1006 |
| YI (Yellowness Index)*) | 0.2 | 0.5 | 0.5 | 0.7 | 0.9 |
| ΔE (Color difference)*) | 0.0 | 0.4 | 0.3 | 0.5 | 0.9 |
| b* (Color coordinate)*) | 0.2 | 0.4 | 0.4 | 0.5 | 0.7 |

*)Low values are desired.

Example A-3: Stabilization of a Polymethylmethacrylate (PMMA) Thick Sheet (1)

70 g of freshly distilled methylmethacrylate are mixed with 70 mg of lauroylperoxide and 105 mg of compound 2. The mixture is degassed and heated in a twist-off glass for 3 hours in a waterbath at 60° C. The prepolymerized syrup is poured between two glass plates, with 1.8 mm distance, which are sealed on three sides. This glass sandwich is kept for 16 hours at 60° C. in an oven, followed by 3 hours at 120° C. The resulting polymethylmethacrylate (PMMA) sheet has a yellowness index of 32.2 (DIN 6167 (1980-01)). This sheet is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table A-3.

TABLE A-3

| | hours | | | | |
|---|---|---|---|---|---|
| | 0 | 257 | 494 | 754 | 986 |
| YI (Yellowness Index)*) | 10.31 | 0.87 | 1.14 | 0.91 | 0.91 |
| ΔE (Color difference)*) | 10.00 | 0.35 | 0.60 | 0.55 | 0.55 |
| b* (Color coordinate)*) | 0.30 | 0.62 | 0.77 | 0.63 | 0.62 |

*)Low values are desired.

Example A-4: Stabilization of a Polymethylmethacrylate (PMMA) Thick Sheet (2)

70 g of freshly distilled methylmethacrylate are mixed with 70 mg of lauroylperoxide, 105 mg of compound 2 and 105 mg of 2-(2H-benzotriazol-2-yl)-6-dodecyl-4-methylphenol (Tinuvin®571). The mixture is degassed and heated in a twist-off glass for 3 hours in a waterbath at 60° C. The prepolymerized syrup is poured between two glass plates, with 1.8 mm distance, which are sealed on three sides. This glass sandwich is kept for 16 hours at 60° C. in an oven, followed by 3 hours at 120° C. The resulting PMMA sheet has a yellowness index of 32.2 (DIN 6167 (1980-01)). This sheet is then exposed to xenon light in accordance to former ASTM G 26 C (Xe light, 2 borosilicate filters "S", 0.35 W/m2 at 340 nm, 63° C.±3° C., 50-60% rel. humidity, continuous light, no water spray). The color is measured in accordance to DIN 6167 (1980-01). The results are shown in Table A-4.

TABLE A-4

| | hours | | | | |
|---|---|---|---|---|---|
| | 0 | 257 | 494 | 754 | 986 |
| YI (Yellowness Index)*) | 0.98 | 1.03 | 1.42 | 1.42 | 1.55 |
| ΔE (Color difference)*) | 0.00 | 0.13 | 0.61 | 0.62 | 0.76 |
| b* (Color coordinate)*) | 0.72 | 0.75 | 0.96 | 0.97 | 1.03 |

*)Low values are desired.

Example A-5: Stabilization of a Polycarbonate/Acrylonitrile Butadiene Styrene (PC/ABS) Plaque 4000 g of PC/ABS (Pulse®A35-105 natural) is cryoground and dried in a vacuum oven at 80° C. for 4 hours. In a Henschel® high-speed mixer the ground polymer is mixed with 4 g of compound 2 and 12 g of 2-(2H-benzotriazol-2-yl)-4,6-bis(1-methyl-1-phenylethyl)phenol (Tinuvin®234). The powder mixture is then compounded on a Berstorff®ZE 25×32D at 270° C. and after drying in a Heliomat²2000 6K drier injection molded on an Engel®EK65 at 260° C. to 2×60×60 mm³ thick plaques. These plaques are exposed to xenon light in accordance to former ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-5.

TABLE A-5

|  | hours | | | | |
| --- | --- | --- | --- | --- | --- |
|  | 0 | 259 | 529 | 742 | 1008 |
| YI (Yellowness Index)*⁾ | 17.3 | 7.3 | 11.8 | 16.2 | 29.3 |
| ΔE (Color difference)*⁾ | 0 | 5.79 | 3.15 | 0.62 | 7.15 |
| b* (Color coordinate)*⁾ | 10.7 | 5.0 | 7.6 | 10.1 | 17.7 |

*⁾Low values are desired.

Example A-6: Stabilization of High Density Polyethylene (HDPE) (1)

4000 g of HDPE (Tipelin®BS 501-17; unstabilized) is mixed with 4 g of compound 2 in a Brabender®PL 2000 for 10 minutes at 200° C. with 30 rpm. The material is then pressed in a pneumatic press at 190° C. for 2 minutes to 1 mm thick plaques which are subjected to the following test a) or b).

a) The plaques obtained are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-6a.

TABLE A-6a

|  | hours | |
| --- | --- | --- |
|  | 0 | 259 |
| YI (Yellowness Index)*⁾ | 2.47 | −1.53 |
| ΔE (Color difference)*⁾ | 0 | 2.14 |
| b* (Color coordinate)*⁾ | 1.63 | −0.42 |

*⁾Low values are desired.

b) The plaques obtained are exposed in an oven with circulating air at 110° C. The color is measured in accordance to DIN 6167 (1980-01). The results are shown in Table A-6b.

TABLE A-6b

| days | 0 | 4 | 7 | 11 | 14 | 18 |
| --- | --- | --- | --- | --- | --- | --- |
| YI (Yellowness Index)*⁾ | 0.67 | 1.79 | 1.88 | 1.72 | 1.72 | 1.72 |
| ΔE (Color difference)*⁾ | 0 | 0.67 | 0.72 | 1.36 | 1.36 | 1.36 |
| b* (Color coordinate)*⁾ | 0.7 | 1.34 | 1.39 | 1.31 | 1.31 | 1.31 |

*⁾Low values are desired.

Example A-7: Stabilization of High Density Polyethylene (HDPE) (2)

4000 g of HDPE (Tipelin®BS 501-17; unstabilized) is mixed with 2 g of compound 2 and 2 g of the condensate of 1-(2-hydroxyethyl)-2,2,6,6-tetramethyl-4-hydroxypiperidine and succinic acid dimethylester (Tinuvin®622) in a Brabender®PL 2000 for 10 minutes at 200° C. with 30 rpm. The material is then pressed in a pneumatic press at 190° C. for 2 minutes to 1 mm thick plaques which are subjected to the following test a) or b).

a) The plaques obtained are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-7a.

TABLE A-7a

|  | hours | |
| --- | --- | --- |
|  | 0 | 259 |
| YI (Yellowness Index)*⁾ | 2.85 | −1.39 |
| ΔE (Color difference)*⁾ | 0 | 2.37 |
| b* (Color coordinate)*⁾ | 1.97 | −0.35 |

*⁾Low values are desired.

b) The plaques obtained are exposed in an oven with circulating air at 110° C. The color is measured in accordance to DIN 6167 (1980-01). The results are shown in Table A-7b.

TABLE A-7b

| days | 0 | 4 | 7 | 11 | 14 | 18 |
| --- | --- | --- | --- | --- | --- | --- |
| YI (Yellowness Index)*⁾ | 3.79 | 9.11 | 9.62 | 8.83 | 8.83 | 8.83 |
| ΔE (Color difference)*⁾ | 0 | 2.97 | 3.26 | 3.32 | 3.32 | 3.32 |
| b* (Color coordinate)*⁾ | 2.48 | 5.41 | 5.69 | 5.20 | 5.20 | 5.20 |

*⁾Low values are desired.

Example A-8: Stabilization of Polypropylene (PP) (1)

2000 g unstabilized PP is mixed with 1 g of 1,3,5-tris(3,5-di-tert-butyl-4-hydroxybenzyl)-1,3,5-triazine-2,4,6(1H,3H,5H)-trione (Irganox®3114), 1 g of tris(2,4-di-tert-butylphenyl)phosphite (Irgafos®168) and 2 g of compound 2 in a high speed mixer and then compounded at 220° C. on a Berstorff®ZE 25×32D twin screw extruder. The composition is injection molded at 230° C. on an Engel®EK 65 into 2×60×60 mm³ plaques which are subjected to the following test a) or b).

a) The plaques obtained are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-8a.

TABLE A-8a

|  | hours | | | | |
| --- | --- | --- | --- | --- | --- |
|  | 0 | 100 | 262 | 504 | 1007 |
| YI (Yellowness Index)*⁾ | 17.7 | 9.2 | 8.8 | 9.3 | 2.2 |
| ΔE (Color difference)*⁾ | 0 | 5.08 | 5.5 | 5.45 | 12.59 |
| b* (Color coordinate)*⁾ | 8.4 | 4.5 | 4.4 | 4.6 | 1.2 |

*⁾Low values are desired.

b) The plaques obtained are exposed in an oven with circulating air at 135° C. The color is measured in accordance to DIN 6167 (1980-01). The results are shown in Table A-8b.

TABLE A-8b

| days | 0 | 1 | 4 | 7 | 10 | 14 |
|---|---|---|---|---|---|---|
| YI (Yellowness Index)*) | 18.1 | 18.1 | 19.7 | 20.4 | 21.1 | 21.7 |
| ΔE (Color difference)*) | 0.0 | 0.9 | 0.8 | 1.2 | 1.5 | 1.9 |
| b* (Color coordinate)*) | 8.6 | 8.5 | 9.3 | 9.7 | 10.1 | 10.4 |

*)Low values are desired.

Example A-9: Stabilization of Polypropylene (PP) (2)

2000 g of unstabilized PP is mixed with 1 g of 1,3,5-tris (3,5-di-tert-butyl-4-hydroxybenzyl)-1,3,5-triazine-2,4,6 (1H,3H,5H)-trione (Irganox®3114), 1 g of tris(2,4-di-tert-butylphenyl)phosphite (Irgafos®168), 1 g of compound 2 and 1 g of Chimassorb®2020 in a high speed mixer and then compounded at 220° C. on a Berstorff®ZE 25×32D twin screw extruder. The composition is injection molded at 230° C. on an Engel®EK 65 into 2×60×60 mm³ plaques which are subjected to the following test a) or b).
Chimassorb®2020:
(Chemical Abstracts No. 192268-64-7)

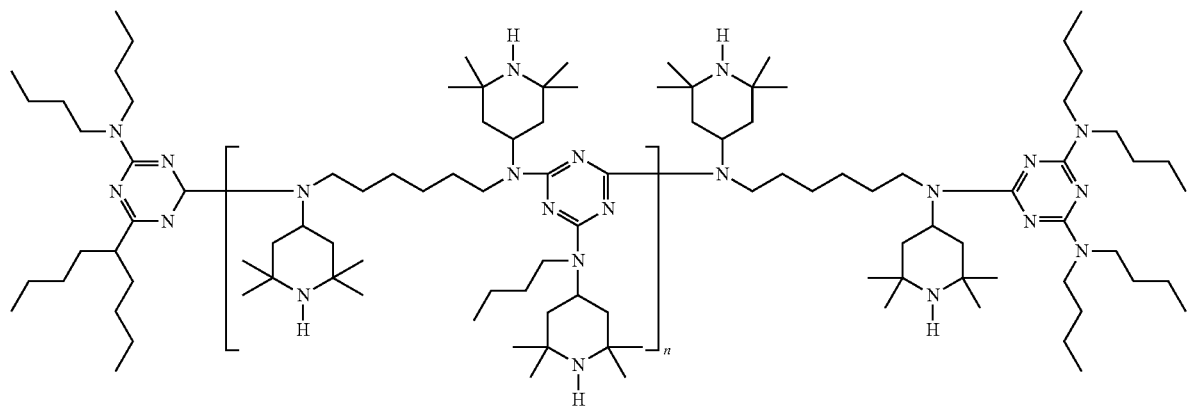

Molecular weight: 2600-3400 g/mol a) The plaques obtained are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-9a.

TABLE A-9a

| | hours | | | | |
|---|---|---|---|---|---|
| | 0 | 100 | 262 | 504 | 1007 |
| YI (Yellowness Index)*) | 17.5 | 8.9 | 8.2 | 8.4 | 8.7 |
| ΔE (Color difference)*) | 0 | 4.9 | 5.44 | 5.43 | 5.68 |
| b* (Color coordinate)*) | 8.6 | 4.4 | 4.0 | 4.1 | 4.4 |

*)Low values are desired.

b) The plaques obtained are exposed in an oven with circulating air at 135° C. The color is measured in accordance to DIN 6167 (1980-01). The results are shown in Table A-9b.

TABLE A-9b

| | days | | |
|---|---|---|---|
| | 0 | 1 | 4 |
| YI (Yellowness Index)*) | 17.4 | 17.3 | 21.1 |
| ΔE (Color difference)*) | 0.0 | 1.1 | 1.9 |
| b* (Color coordinate)*) | 8.6 | 8.5 | 10.0 |

*)Low values are desired.

Example A-10: Stabilization of Polypropylene (PP) (3)

2000 g of unstabilized PP is mixed with 1 g of 1,3,5-tris (3,5-di-tert-butyl-4-hydroxybenzyl)-1,3,5-triazine-2,4,6 (1H,3H,5H)-trione (Irganox®3114), 1 g of tris(2,4-di-tert-butylphenyl)phosphite (Irgafos®168), 1 g of compound 2 and 1 g of the condensate of 1-(2-hydroxyethyl)-2,2,6,6-tetramethyl-4-hydroxypiperidine and succinic acid dimethylester (Tinuvin®622) in a high speed mixer and then compounded at 220° C. on a Berstorff®ZE 25×32D twin screw extruder. The composition is injection molded at 230° C. on an Engel®EK 65 to 2×60×60 mm³ plaques which are subjected to the following test a) or b).

a) The plaques are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-10a.

TABLE A-10a

| | hours | | | | |
|---|---|---|---|---|---|
| | 0 | 100 | 262 | 504 | 1007 |
| YI (Yellowness Index)*) | 19.8 | 9.4 | 8.6 | 8.5 | 6.1 |
| ΔE (Color difference)*) | 0 | 5.97 | 6.55 | 6.65 | 9.37 |
| b* (Color coordinate)*) | 9.5 | 4.7 | 4.2 | 4.2 | 3.1 |

*)Low values are desired.

b) The plaques obtained are exposed in an oven with circulating air at 135° C. The color is measured in accordance to DIN 6167 (1980-01). The results are shown in Table A-10b.

TABLE A-10b

| | days | | | | |
|---|---|---|---|---|---|
| | 0 | 1 | 4 | 7 | 10 |
| YI (Yellowness Index)*) | 19.7 | 19.6 | 21.1 | 22.4 | 23.8 |
| ΔE (Color difference)*) | 0.0 | 0.8 | 0.8 | 1.3 | 2.0 |
| b* (Color coordinate)*) | 9.4 | 9.2 | 10.0 | 10.7 | 11.3 |

*)Low values are desired.

Example A-11: Stabilization of Polybutadiene Terephthalate (PBT) (1)

2500 g of PBT (Crastin®6134) is cryo-ground and dried in a vacuum oven at 80° C. for 4 hours. In a Henschel® high-speed mixer the ground polymer is mixed with 1.25 g of ethylenebis(oxyethylene)bis-(3-(5-tert-butyl-4-hydroxy-m-tolyl)-propionate) (Irganox®245), 3.75 g of tris(2,4-di-tert-butylphenyl)phosphite (Irgafos®168), 12.5 g of 2-(2H-benzotriazol-2-yl)-4,6-bis(1-methyl-1-phenylethyl)phenol (Tinuvin®234) and 2.5 g of compound 2. The powder mixture is then compounded on a Berstorff®ZE 25×32D at 245° C. and after drying in a Heliomat®2000 6K drier injection molded on an Engel®EK65 at 250° C. to 2×60×60 mm³ thick plaques. These plaques are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-11.

TABLE A-11

| | hours | | | |
|---|---|---|---|---|
| | 0 | 100 | 243 | 500 |
| YI (Yellowness Index)*) | 32.2 | 35.9 | 39.1 | 42.2 |
| ΔE (Color difference)*) | 0 | 2.3 | 4.1 | 5.9 |
| b* (Color coordinate)*) | 17.2 | 19.5 | 21.2 | 23.0 |

*)Low values are desired.

Example A-12: Stabilization of Polybutadiene Terephthalate (PBT) (2)

2500 g of PBT (Crastin®6134) is cryo-ground and dried in a vacuum oven at 80° C. for 4 hours. In a Henschel® high-speed mixer the ground polymer is mixed with 1.25 g of ethylenebis(oxyethylene)bis-(3-(5-tert-butyl-4-hydroxy-m-tolyl)-propionate) (Irganox®245), 3.75 g tris(2,4-di-tert-butylphenyl)phosphite (Irgafos®168), 12.5 g 2-(2H-benzotriazol-2-yl)-4,6-bis(1-methyl-1-phenylethyl)phenol (Tinuvin®234), 1.25 g of the condensate of 1-(2-hydroxy-ethyl)-2,2,6,6-tetramethyl-4-hydroxypiperidine and succinic acid dimethylester (Tinuvin®622) and 1.25 g of compound 2. The powder mixture is then compounded on a Berstorff®ZE 25×32D at 245° C. and after drying in a Heliomat®2000 6K drier injection molded on an Engel®EK65 at 250° C. to 2×60×60 mm³ thick plaques. These plaques are exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-12.

TABLE A-12

| | hours | | | |
|---|---|---|---|---|
| | 0 | 100 | 243 | 500 |
| YI (Yellowness Index)*) | 32.8 | 36.2 | 39.2 | 42.1 |
| ΔE (Color difference)*) | 0 | 2.1 | 3.8 | 5.5 |
| b* (Color coordinate)*) | 17.8 | 19.9 | 21.5 | 23.1 |

*)Low values are desired.

Example A-13: Stabilization of a Polyurethane (PUR) Soft Foam a) Preparation of the Polyether/Polyurethane Soft Foams:

0.71 g (0.45% by weight based on the polyol) of anti-scorch stabilizer Irgastab®PUR 68 of BASF and 4.73 g (3.00% by weight referred to polyol) of the light stabilizer composition listed in Table A-13a are dissolved in 157.1 g of a polyether polyol (Lupranol®2074 of BASF, trifunctional polyether polyol containing predominantly secondary hydroxyl groups; hydroxyl number 48 mg KOH/g, water content less than 0.1%, acid number less than 0.06 mg KOH/g), 9.84 g of a solution consisting of 1.89 g of Tegostab®BF 2370 (a silicone surfactant of Evonik Industries), 0.24 g of Tegoamin®33 (amine catalyst of Evonik Industries, 33% by weight of triethylenediamine and 67% by weight of dipropyleneglycol) and 7.5 g of deionized water are added and the reaction mixture is stirred vigorously for 10 seconds at 2600 rpm. 0.31 g Kosmos®29 (catalyst based on stannous octoate of Evonik Industries) is then added and the reaction mixture is again stirred vigorously for 18 seconds at 2600 rpm. 92.19 g of an isocyanate [Lupranat®T80 of BASF; toluene-2,4- and toluylene-2,6-diisocyanate mixture] is then added with continuous stirring for 5 to 7 seconds at 2600 rpm. The mixture is then poured into a 20×20×20 cm³ cake-box and the exothermic temperature is measured during foaming to a foam block. The foam blocks are cooled and stored at room temperature for 24 hours. The next day the foams are cut into 4.4 cm×3 cm×1 cm specimens for the weathering tests.

TABLE A-13a

| PUR | Light stabilizer mixture |
|---|---|
| PUR 1 | 2.365 g of compound 2 and 2.365 g of stabilizer 1 |
| PUR 2 | 2.365 g of compound 2 and 2.365 g of stabilizer 2 |
| PUR 3 | 2.365 g of compound 2 and 2.365 g of stabilizer 3 |

Stabilizer 1: 2-(2H-benzotriazol-2-yl)-6-dodecyl-4-methylphenol (Tinuvin ®571)
Stabilizer 2: Reaction product of methyl 3-(3-(2H-benzotriazole-2-yl)-5-t-butyl-4-hydroxyphenyl)propionate/polyethyleneglykol 300 (Tinuvin ®213)
Stabilizer 3: Mixture of 95% of 3-(2H-benzotriazol-2-yl)-5-(1,1-dimethylethyl)-4-hydroxybenzenepropanoic acid $C_7$-$C_9$alkylester and 5% of 1-methoxy-2-propyl acetate (Tinuvin ®384-2)

b) Weathering is used in order to assess the foam stability upon light exposure. The foam samples are put in the weathering chamber and are exposed according to ASTM G 155-Cycle 4. The color change is determined as a function of time. The foam color quality is reported in terms of Yellowness Index (YI) determined on the foam samples in accordance with the ASTM 1926-70. The results are listed in Table A-13b.

TABLE A-13b

| PUR | | 0 | 3 | 6 | 9 | 12 | 18 | 24 |
|---|---|---|---|---|---|---|---|---|
| PUR 1 | YI*) | −0.9 | 4.5 | 8.4 | 13.8 | 15.5 | 18.6 | 24.7 |
| PUR 2 | YI*) | −0.5 | 5.5 | 8.9 | 15.0 | 16.0 | 18.3 | 26.6 |
| PUR 3 | YI*) | −0.4 | 4.7 | 9.4 | 14.5 | 15.2 | 19.9 | 26.0 |

*)Low values are desired.

Column header: hours

Example A-14: Stabilization of Thermoplastic Polyurethane (TPU)

a) 3000 g of cryoground TPU (Desmopan®385 E) are dried in a vacuum oven at 80° C. for 12 hours. In a Henschel® mixer heated to 80° C. the polymer is mixed with the stabilizer system indicated in Table A-14a and then compounded on a twin screw extruder Berstorff®ZE 25×32D at 2100 C. After drying with a hot air drier the compounds are injection molded on a Engel®HL 60 machine into 2×44×68 mm³ plaques.

TABLE A-14a

| TPU | Stabilizer system |
|---|---|
| TPU 1 | 10.2 g of Irganox ®1010, 4.8 g of Irgafos ®126, 45 g of compound 2 and 45 g of Tinuvin ®PA 328 |
| TPU 2 | 10.2 g of Irganox ®1010, 4.8 g of Irgafos ®126, 45 g of compound 2 and 45 g of Tinuvin ®571 |
| TPU 3 | 10.2 g of Irganox ®1010, 4.8 g of Irgafos ®126, 45 g of compound 2 and 45 g of Tinuvin ®213 |

Irganox ®1010: Pentaerythritol tetrakis[3-(3,5-di-tert-butyl-4-hydroxyphenyl)propionate]
Irgafos ®126: Bis[2,4-di-tert-butylphenyl] pentaerythritol diphosphite
Tinuvin ®PA 328: 2-(2H-benzotriazol-2-yl)-4,6-bis(1,1-dimethylpropyl)phenol
Tinuvin ®571: 2-(2H-benzotriazol-2-yl)-6-dodecyl-4-methylphenol
Tinuvin ®213: Reaction product of methyl 3-(3-(2H-benzotriazole-2-yl)-5-t-butyl-4-hydroxyphenyl)propionate/polyethyleneglykol 300 b) These plaques are exposed to xenon light in accordance to former ISO 105 B 06 (Xe light, inner filter borosilicate "S" and outer filter sodalime, 0.45 W/m2 at 340 nm, 100° C.±3° C., 20-30% rel. humidity, continuous light, no water spray). The color is measured in accordance to DIN 6167 (1980-01). The results are shown in Table A-14b.

TABLE A-14b

| TPU | | 0 | 8 | 24 | 48 | 96 |
|---|---|---|---|---|---|---|
| TPU 1 | YI*) | 13.62 | 13.09 | 13.15 | 13.22 | 14.46 |
| TPU 2 | YI*) | 11.61 | 10.56 | 10.69 | 11.08 | 13.18 |
| TPU 3 | YI*) | 11.88 | 10.64 | 10.79 | 11.46 | 12.71 |

Column header: hours

*)Low values are desired for the yellowness index (YI).

Example A-15: Stabilization of Flexible Polyvinyl Chloride (f-PVC)

A base mixture of 64.73 phr PVC (Norvinyl®S7060 of Ineos), 32.36 phr diisononylphthalate plasticizer (Palatinol®N of BASF), 1.61 phr epoxidized soybean oil (Drapex®39 of Galata Chem.) and 1.30 phr heat stabilizer (Baerostab®CT 9051×RF of Baerlocher; liquid CaZn stabilizer) is prepared (phr means parts per hundred rubber). 40 g of this PVC blend is mixed with 0.1 g of 2-hydroxy-4-octyloxybenzophenone (Chimassorb®81) and 0.1 g of compound 2 in a glass beaker and then calendered for 8 minutes at 160° C. with f=1:1.2 on a two roll mill with a gap width of 0.4 mm. The sheets obtained are then exposed to xenon light in accordance to ASTM G 155 Cycle 1 (Xe light, 2 borosilicate filters "S", 0.35 W/m2 at 340 nm, 63° C.±3° C., 50-60% rel. humidity, continuous light, 102 minutes dry followed by 18 minutes water spray). The color is measured in accordance to DIN 6167 (1980-01). The results are shown in Table A-15.

TABLE A-15

| hours | 0 | 243 | 500 | 1005 | 1501 |
|---|---|---|---|---|---|
| YI (Yellowness Index)*) | 3.2 | 2.0 | 2.1 | 2.0 | 2.4 |
| ΔE (Color difference)*) | 0 | 0.7 | 0.6 | 0.7 | 0.4 |
| b* (Color coordinate)*) | 1.9 | 1.2 | 1.3 | 1.3 | 1.5 |

*)Low values are desired.

The invention claimed is:

1. A compound having the formula (I)

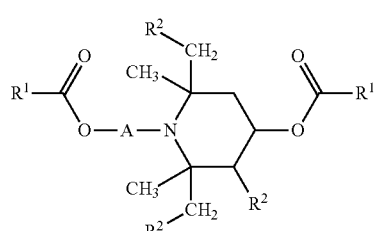

(I)

wherein
A is —CH($R^3$)—$CH_2$— or —$CH_2$— CH($R^3$)—;
each $R^1$ is the same and is $C_1$-$C_{21}$ alkyl or $C_3$-$C_7$ cycloalkyl;
$R^2$ is H or $C_1$-$C_3$ alkyl; and
$R^3$ is H or $C_1$-$C_4$ alkyl.

2. The compound according to claim 1, wherein each $R^1$ is $C_1$-$C_{17}$ alkyl.

3. The compound according to claim 1, wherein each $R^1$ is selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, and $C_{17}$ alkyl.

4. The compound according to claim 1, wherein each $R^1$ is $C_1$-$C_{21}$ alkyl substituted with at least one substituent selected from $C_1$-$C_4$ alkoxy and —OH.

5. The compound according to claim 1, wherein $R^2$ is H.

6. The compound according to claim 1, wherein A is —$CH_2$—$CH_2$—, —CH($CH_3$)—$CH_2$—, or —$CH_2$—CH($CH_3$)—.

7. A compound of the formula

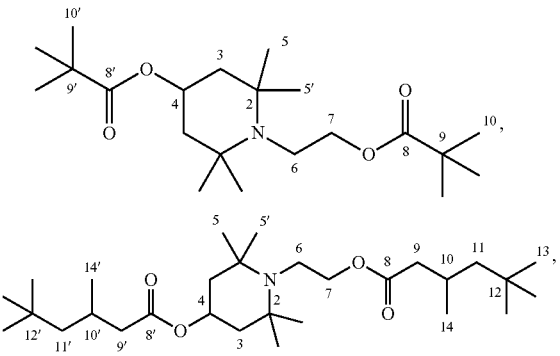

Bis-(1-octyloxy-2,2,6,6-tetramethyl-4-piperidinyl)sebacate;

condensate of 1-(2-hydroxyethyl)-2,2,6,6-tetramethyl-4-hydroxypiperidine and succinic acid dimethylester;

2,2'-methylenebis(6-(2H-benzotriazol-2-yl)-4-1,1,3,3-tetramethylbutyl)phenol;

2-(2H-benzotriazol-2-yl)-6-dodecyl-4-methylphenol;

2-(2H-benzotriazol-2-yl)-4,6-bis(1-methyl-1-phenylethyl)phenol;

1,3,5-tris(3,5-di-tert-butyl-4-hydroxybenzyl)-1,3,5-triazine-2,4,6(1H,3H,5H)-trione;

tris(2,4-di-tert-butylphenyl)phosphite;

ethylenebis(oxyethylene)bis-(3-(5-tert-butyl-4-hydroxy-m-tolyl)-propionate);

reaction product of methyl 3-(3-(2H-benzotriazole-2-yl)-5-t-butyl-4-hydroxyphenyl)propionate/polyethyleneglykol 300;

3-(2H-benzotriazol-2-yl)-5-(1,1-dimethylethyl)-4-hydroxybenzenepropanoic acid $C_7$-$C_9$alkylester, optionally in admixture with 1-methoxy-2-propyl acetate;

pentaerythritol tetrakis[3-(3,5-di-tert-butyl-4-hydroxyphenyl)propionate];

Bis[2,4-di-tert-butylphenyl] pentaerythritol diphosphate;

2-(2H-benzotriazol-2-yl)-4,6-bis(1,1-dimethylpropyl)phenol;

Reaction product of methyl 3-(3-(2H-benzotriazole-2-yl)-5-t-butyl-4-hydroxyphenyl)propionate/polyethyleneglykol 300; or a compound of the formula wherein n is a number such that the molecular weight is from 2600 to 3400 g/mol.

14. A coated article which is coated with the composition according to claim 8.

8. A composition comprising the compound according to claim 1 and an organic material.

9. The composition according to claim 8, in the form of a coating composition.

10. The composition according to claim 8, wherein the organic material is a polyethylene or polypropylene or polyurethane or styrenic polymer or a polyvinylchloride.

11. The composition according to claim 8, which further comprises one or more UV absorbers of the hydroxyphenyl-benzotriaziole or hydroxy-phenyl-triazine or hydroxyl-benzophenone or oxanilide class or cyanoacrylate or malonate and combinations thereof.

12. The composition according to claim 8, which further comprises a sterically hindered amine compound.

13. The composition according to claim 8, which further comprises one or more of the following compounds:

15. A coated article which is coated with a composition comprising the compound according to claim 1 and an organic material comprising a metal substrate, and coat comprising
   a) a primer coat which is electrodeposited onto the metal substrate;
   b) at least one pigmented base coat which is in direct contact with the primer coat, and a clear coat that is in direct contact with the pigmented base coat and comprises a compound of claim 1.

16. A light stabilizer comprising the compound according to claim 1.

17. A process for preparing a coating on a substrate which comprises coating the substrate with the compound according to claim 1.

18. The process according to claim 17, wherein the substrate is a metal, metal alloy, woods, plastic, ceramic or another coating.

19. The compound according to claim 1, wherein each $R^1$ is $C_3$-$C_{12}$ alkyl.

20. The compound according to claim 1, wherein each $R^1$ is $C_3$-$C_6$ cycloalkyl.

* * * * *